(12) United States Patent
Framroze et al.

(10) Patent No.: US 11,135,220 B1
(45) Date of Patent: Oct. 5, 2021

(54) METHODS OF TREATING VIRAL INFECTIONS WITH FORMULATED COMPOSITIONS COMPRISING 4-METHYL-5-(PYRAZIN-2-YL)-3H-1,2-DITHIOLE-3-THIONE

(71) Applicant: ST IP Holding AG, Zug (CH)

(72) Inventors: Bomi Framroze, Menlo Park, CA (US); Jeffrey A. Gelfand, Cambridge, MA (US)

(73) Assignee: ST IP Holding AG, Zug (CH)

(*) Notice: Subject to any disclaimer, the term of this patent is extended or adjusted under 35 U.S.C. 154(b) by 0 days.

(21) Appl. No.: 16/844,981

(22) Filed: Apr. 9, 2020

Related U.S. Application Data

(60) Provisional application No. 63/007,332, filed on Apr. 8, 2020.

(51) Int. Cl.
*A61K 31/497* (2006.01)
*A61K 9/10* (2006.01)

(52) U.S. Cl.
CPC .............. *A61K 31/497* (2013.01); *A61K 9/10* (2013.01)

(58) Field of Classification Search
CPC .................................................. A61K 31/497
See application file for complete search history.

(56) References Cited

U.S. PATENT DOCUMENTS

| | | | |
|---|---|---|---|
| 5,691,338 A * | 11/1997 | Prochaska | A61K 31/385 514/252.01 |
| 7,012,148 B2 | 3/2006 | Curphey | |
| 7,067,116 B1 | 6/2006 | Bess et al. | |
| 7,199,122 B2 | 4/2007 | Ruggeri et al. | |
| 7,288,652 B2 | 10/2007 | Kim et al. | |
| 7,452,884 B2 | 11/2008 | Ruggeri et al. | |
| 7,648,712 B2 | 1/2010 | Bess et al. | |
| 7,803,353 B2 | 9/2010 | Lee et al. | |
| 7,959,958 B2 | 6/2011 | Furrer et al. | |
| 8,142,806 B2 | 3/2012 | Gupta et al. | |
| 8,461,136 B2 | 6/2013 | Fahl et al. | |
| 8,481,762 B2 | 7/2013 | Commo | |
| 8,664,261 B2 | 3/2014 | Furrer | |
| 8,858,995 B2 | 10/2014 | Gupta et al. | |
| 8,920,864 B2 | 12/2014 | Spence et al. | |
| 9,308,192 B2 | 4/2016 | Coulombe et al. | |
| 9,314,419 B2 | 4/2016 | Lin et al. | |
| 9,370,504 B2 | 6/2016 | Kim et al. | |
| 9,452,982 B2 | 9/2016 | Bell et al. | |
| 9,839,638 B2 | 12/2017 | Fahl et al. | |
| 9,974,740 B2 | 5/2018 | Spence et al. | |
| 2005/0163855 A1 | 7/2005 | Cho et al. | |
| 2006/0106079 A1 | 5/2006 | Kim et al. | |
| 2014/0343092 A1 | 11/2014 | Haydar et al. | |
| 2015/0359739 A1 | 12/2015 | Bunick et al. | |
| 2016/0206641 A1 | 7/2016 | Singh | |

FOREIGN PATENT DOCUMENTS

| | | | |
|---|---|---|---|
| AU | 199537603 A1 | 4/1996 | |
| AU | 2003284758 A1 | 6/2004 | |
| CA | 2718152 A1 | 9/2008 | |
| CN | 100366619 C | 2/2008 | |
| EP | 1474131 A1 | 11/2004 | |
| EP | 1565460 A1 | 8/2005 | |
| EP | 1696958 A1 | 9/2006 | |
| EP | 1803468 A1 | 7/2007 | |
| EP | 2810564 B1 | 6/2017 | |
| JP | 2006511508 A | 4/2006 | |
| KR | 100491318 B1 | 5/2005 | |
| KR | 2018123796 A | 11/2018 | |
| WO | WO 1997/03055 A1 | 1/1997 | |
| WO | WO 200185142 A1 | 11/2001 | |
| WO | WO 2004048369 A1 | 6/2004 | |
| WO | WO 2005070397 A1 | 8/2005 | |
| WO | WO 2008110585 A2 | 9/2008 | |
| WO | WO 2012170676 A1 | 12/2012 | |
| WO | WO 2016043533 A1 | 3/2013 | |
| WO | WO 2014100403 A1 | 6/2014 | |
| WO | WO 2016207914 A2 | 12/2016 | |
| WO | WO 2017109599 A1 | 6/2017 | |
| WO | WO 2017168263 A1 | 10/2017 | |
| WO | WO-2018047013 A1 * | 3/2018 | ............. A61K 47/32 |

OTHER PUBLICATIONS

Chi et al. ("Oltipraz, a novel inhibitor of hepatitis B virus transcription through elevation of p53 protein", Carcinogenesis, 1998, vol. 19, No. 12, pp. 2133-2138) (Year: 1998).*

Ciotti et al. (Chemotherapy, 2019, vol. 64, pp. 215-223) (Published Online Apr. 7, 2020) (Year: 2019).*

Cao et al. (N. Engl. J. Med. May 7, 2020;382(19): 1787-1799) (Year: 2020).*

Liu, P. (2013) Nanocrystal formulation for poorly soluble drugs. Dissertationes bioscientiarum molecularium Universitatis Helsingiensis in Viikki, Dec. 2013, pp. 62 (Year:2013).

Kochar et al., "Oltipraz Provides Protection to Swiss Albino Mice Against Gamma Radiation", Pharmacologyonline, Universita Degli Studi Di Salerno, IT, vol. 2, Jan. 1, 2010, pp. 39-44.

* cited by examiner

*Primary Examiner* — James D. Anderson
(74) *Attorney, Agent, or Firm* — Hoffmann & Baron, LLP

(57) ABSTRACT

This disclosure provides, among other things, formulated oltipraz compositions comprising stabilized oltipraz crystals, for use in treating a patient who has a viral infection or is at risk of incurring a viral infection. Such viral infections can include a viral infection caused by a coronavirus such as one associated with MERS or SARS, e.g., SARS-CoV-2.

20 Claims, No Drawings

METHODS OF TREATING VIRAL INFECTIONS WITH FORMULATED COMPOSITIONS COMPRISING 4-METHYL-5-(PYRAZIN-2-YL)-3H-1,2-DITHIOLE-3-THIONE

CROSS-REFERENCE TO RELATED APPLICATIONS

This application claims the benefit of U.S. Provisional Application No. 63/007,332, filed Apr. 8, 2020, the contents of which application is incorporated herein by reference in its entirety.

FIELD

The disclosure herein relates to the use of formulated compositions comprising the compound 4-methyl-5-(pyrazin-2-yl)-3H-1,2-dithiole-3-thione (also known as oltipraz) for use in treating individuals who have or are at risk of incurring a viral infection such as a coronavirus infection.

BACKGROUND

A coronavirus is a common type of virus that can infect the nose, sinuses, or upper throat. Coronavirus infections are common and can spread much like other viruses that inflict a cold or flu. Although most coronaviruses are relatively benign, some can be deadly, e.g., those that cause Middle East respiratory syndrome (MERS) or severe acute respiratory syndrome (SARS). The virus that causes COVID-19, i.e., "respiratory syndrome coronavirus 2" or "SARS-CoV-2", is genetically related to the coronavirus that caused the outbreak of Severe Acute Respiratory Syndrome (SARS) in 2003, but the disease that SARS-CoV-2 causes is different. Two different types of SARS-CoV-2 viruses have been identified, namely type L (accounting for 70 percent of the strains) and type S (accounting for 30 percent).

These symptoms of COVID-19 typically may appear 5-14 days after exposure and can include fever, cough, shortness of breath, perspiration. Onset of serious lung damage or even death can occur rapidly following infection. Emergency warning signs include trouble breathing, persistent pain or pressure in the chest, new confusion or inability to arouse and bluish lips or face. Given the severity of the symptoms and potential effects, there exists a need for treatments to combat viral infections and/or prepare individuals to withstand such a viral infection and the symptoms associated with it.

DETAILED DESCRIPTION

The compound 4-methyl-5-(pyrazin-2-yl)-3h-1,2-dithiole-3-thione, also known as oltipraz, confers cytoprotection by triggering nuclear factor related erythroid factor-2 (Nrf2)-dependent gene expression. Oltipraz has been described as having various properties, e.g., as an antimicrobial compound that controls schistosomiasis, as an anti-tumor agent, as a chemo-protectant, and as a compound to help control chemo-radiation induced mucositis.

Oltipraz is known to exist in crystalline form. To date, known crystalline oltipraz formulations, which are prepared by recrystallizing oltipraz (see, e.g., WO2016207914), comprise a mixture of oltipraz crystals of varying sizes up to millimeters in length along the longest axis, which crystals are highly insoluble in water and have poor bioavailability when administered topically or orally.

The properties (e.g., biological and/or solubility) of crystalline oltipraz can be improved by formulating compositions in which crystal parameters including particle size are controlled and stabilized. Such compositions are described in International Application PCT/IB2017/001312 ("the '1312 PCT"), filed Sep. 12, 2017 ("Formulations of 4-Methyl-5-(Pyrazin-2-yl)-3H-1,2-Dithiole-3-Thione, and Methods of Making and Using Same") (published as WO 2018/047013), the disclosure of which is incorporated herein by reference. The compositions comprising the stabilized oltipraz crystals disclosed in the '1312 PCT are generally referred to herein as "formulated oltipraz compositions." By controlling the crystal particle size and formulation, crystals of oltipraz are provided that have prolonged size-stability in aqueous suspension and improved aqueous solubility as compared to previously known forms of oltipraz such as recrystallized oltipraz prepared according to the process disclosed in U.S. Pat. No. 4,110,450 or in PCT/IN2016/050197 to Framroze (published as WO 2016/207914 A2). For example, the stabilized oltipraz crystals are of a controlled, much smaller size and have beneficial properties such as excellent stability in the form of a dry composition and/or the ability to be readily re-suspended in aqueous compositions to form substantially homogeneous dispersions of oltipraz crystals that typically exhibit substantially improved solubility, size-stability and/or efficacy compared to other forms of oltipraz known in the art. The formulated oltipraz compositions have been found to reduce mucositis in animal models, and decrease reactive oxygen species in in vitro assays significantly better than recrystallized oltipraz. See, e.g., the '1312 PCT application, and also PCT/IB2019/000235 ("the '0235 PCT") to Framroze and Gelfand (published as WO 2019/171174 A2). The disclosures of the '1312 PCT and the '0235 PCT applications pertaining to the in vivo and in vitro tests and results described in the examples and figures therein are expressly incorporated herein by reference.

It has been discovered that the formulated oltipraz compositions described herein can be used for the prophylaxis or treatment of a patient who has a viral infection, including an infection from a coronavirus such as one associated with MERS or SARS (e.g., SARS-CoV-2, including type L and type S strains). The formulated oltipraz compositions can be administered to reduce an infected patient's symptoms, and/or to treat an infected patient with mild illness symptoms with the goal of preventing progression into severe disease.

The formulated oltipraz compositions described herein can be used to treat an individual who has a viral infection, including, e.g., one that is caused by a coronavirus such as one associated with MERS or SARS (e.g., SARS-CoV-2, including type L and type S strains), Treatment with such compositions can reduce the maximum severity of symptoms experienced by the individual if taken prior to or at the outset of the infection, and/or reduce or eliminate the symptoms and/or effects if taken after the viral infection has begun. Alternatively, or in addition, the pharmaceutical formulations, compositions, devices and therapies described herein may be used to pre-treat an individual who is at risk of a viral infection such as a coronavirus infection, e.g., one associated with MERS or SARS (e.g., SARS-CoV-2, including type L and type S strains) in order to lessen the likelihood that an infection may occur or to prepare the individual to better withstand a viral infection if it does occur. Such "host hardening" in advance of a viral infection can reduce the severity of, or eliminate, some or all of the effects and/or symptoms experienced by the individual in the event that he/she experiences a viral infection such as COVID-19. Such pre-treatment can be especially beneficial for persons at risk from such viral infections e.g., individuals having hypertension, decreased pulmonary function, or respiratory diseases or conditions such as pneumonia.

While not wishing to be bound by any particular mode of action, it is believed that the formulated oltipraz compositions can provide such benefits vis-à-vis SARS-CoV-2 or other coronavirus, e.g., by (i) reducing entry of the SARS-CoV-2 or other virus into host cells and (ii) protecting respiratory epithelium and alveolar pneumocytes from reactive oxygen species ("ROS")-mediated damage.

The stabilized oltipraz crystals in the formulated oltipraz compositions described herein and in the '1312 PCT can have a MHD of from 30 to 2000 nm. As described in the '1312 PCT and in more detail below, the term 'MHD' is a measure of particle size and refers to the intensity averaged, mean hydrodynamic diameter (Z-average) as determined by the cumulants fitting of dynamic light scattering. Such stabilized oltipraz crystals have improved solubility in aqueous solution compared to previous crystal forms of oltipraz and when comprised in pharmaceutical compositions provide for increased therapeutic efficacy.

The stabilized oltipraz crystals in the formulated oltipraz compositions can have an intensity averaged, mean hydrodynamic diameter (Z-average) as determined by dynamic light scattering (DLS) in a range of from 30 to 2000 nm. (For convenience, in this disclosure the dimension of "intensity averaged, mean hydrodynamic diameter (Z-average) as determined by the cumulants fitting of dynamic light scattering" data is abbreviated as "MHD" and the precise method by which DLS measurements can be made to determine the MHD are provided below.) Usually, the stabilized oltipraz crystals have a MHD of from 30 to 1200 nm; more often from 100 to 700 nm and still more typically from 150 to 450 nm or from 400 nm to 700 nm or from 400 nm to 600 nm. In certain embodiments, the stabilized oltipraz crystals have a MHD within a target range of from 30 to 100, 100 to 1200 nm, 150 to 600 nm, 150 to 450 nm, 400 nm to 700 nm, 400 nm to 600 nm, 300 to 800 nm, or 450 to 550 nm.

A. Stabilized Oltipraz Crystals and Formulated Oltipraz Compositions

As noted above, the formulated oltipraz compositions comprise stabilized oltipraz crystals having an MHD in the range of from 30 to 2000 nm, such as from 30 to 1200 nm, e.g. 100 to 600 nm, 400 to 700 nm, 400 to 600 nm, 300 to 800 nm, 400 to 800 nm, 450 to 550 nm, 700 to 900 nm, or 900 to 1200 nm. Because such formulated oltipraz compositions may be used in accordance with the compositions and methods of this disclosure, they are described herein in this Section A.

Certain embodiments of the formulated oltipraz compositions and methods described herein comprise a quantity of crystals of 4-methyl-5-(pyrazin-2-yl)-3H-1,2-dithiole-3-thione having an MHD in the range of from 30 to 1200 nm, with embodiments having MHD's within target ranges of from 30 to 100, 100 to 200 nm, 100 to 300 nm, 100 to 1200 nm, 150 to 600 nm, 150 to 450 nm, 300 to 800 nm, 300 to 600 nm, 400 to 700 nm, 400 to 600 nm, 450 to 550 nm, 700 to 900 nm, or 900 to 1200 nm. The MHD of the crystals may be measured in any number of ways known to skilled artisans, including dynamic light scattering as described herein. As mentioned above, the oltipraz can be prepared in crystalline form. Embodiments of the formulated oltipraz compositions provided herein have been found to provide dry compositions of oltipraz crystals that are stable for extended periods, and which are able to be readily resuspended in aqueous compositions to form substantially homogeneous dispersions of oltipraz crystals that exhibit substantially improved properties as compared to the previously available crystalline form.

Formulated oltipraz compositions that may be used in the products and processes described herein typically also exhibit substantially increased rate of dissolution and solubility in water, e.g., at 20° C., as compared to oltipraz crystals prepared from standard methods (e.g., ranging from 20 µm to 200 µm or greater). For example, the stabilized oltipraz crystals in the compositions of this disclosure typically have a solubility in water at 20° C. between 100 and about 250% that of crystals of oltipraz, prepared from recrystallization and having diameters of 20 to 200 µm. More typically, stabilized oltipraz crystals useful in the compositions and processes of this disclosure have a solubility of from about 130 to about 220%, such as from about 160% to about 200% (e.g. from about 170 to about 190%) that of oltipraz crystals of 20 to 200 µm in diameter.

The solubility of oltipraz in water at 20° C. in certain embodiments of compositions disclosed herein is almost double that of the larger oltipraz crystals (e.g., a >80% increase). Solubility values of >3.5 µg/ml, >4.0 µg/ml, >4.5 µg/ml, >5.0 µg/ml and >5.5 µg/ml are all possible, including, e.g., about 5.1 µg/ml, about 5.2 µg/ml, about 5.3 µg/ml, about 5.4 µg/ml, about 5.5 µg/ml, about 5.6 µg/ml, and about 5.7 µg/ml. Hence, solubility values in water at 20° C. in the following exemplary ranges are possible: 3.5 µg/ml to 8.0 µg/ml, 3.5 µg/ml to 7.0 µg/ml, 3.5 µg/ml to 6.0 µg/ml, 3.5 µg/ml to 5.7 µg/ml, 4.0 µg/ml to 8.0 µg/ml, 4.0 µg/ml to 7.0 µg/ml, 4.0 µg/ml to 6.0 µg/ml, 4.0 µg/ml to 5.7 µg/ml, 4.5 µg/ml to 8.0 µg/ml, 4.5 µg/ml to 7.0 µg/ml, 4.5 µg/ml to 6.0 µg/ml, 4.5 µg/ml to 5.7 µg/ml, 5.0 µg/ml to 8.0 µg/ml, 5.0 µg/ml to 7.0 µg/ml, 5.0 µg/ml to 6.0 µg/ml, 5.0 µg/ml to 5.7 µg/ml, 5.5 µg/ml to 8.0 µg/ml, 5.5 µg/ml to 7.0 µg/ml, 5.5 µg/ml to 6.0 µg/ml, 5.5 µg/ml to 5.7 µg/ml, 6.0 µg/ml to 6.5 µg/ml, 6.0 µg/ml to 7.0 µg/ml, 6.0 µg/ml to 8.0 µg/ml, 6.5 µg/ml to 7.0 µg/ml, 6.5 µg/ml to 8.0 µg/ml, 7.0 µg/ml to 8.0 µg/ml, and greater than 8.0 µg/ml.

Typically, therefore, the formulated oltipraz compositions that are described in this Section A will have a solubility in water at 20° C. of from about 3.5 to about 8 µg/ml, more typically from about 4 to about 7.5 µg/ml, such as from about 4.5 to about 7 µg/ml (e.g. from about 5 to about 6.5 µg/ml, such as from about 5.5 to about 6 µg/ml, e.g. about 5.7 µg/ml).

The stabilized oltipraz crystals described in this Section A can be prepared by processing oltipraz into crystals as described in the '1312 PCT having the desired size range using processes as described below. The disclosure of the '1312 PCT relating to preparing such stabilized oltipraz crystals is expressly incorporated herein by reference. In some circumstances, once the desired size is attained, however, the crystals in aqueous or other liquid solution will tend to grow larger over time, e.g., by agglomerating and/or recrystallizing to form larger crystals. Hence, in instances where it is desired to prevent the crystals from growing larger for a period of time, at least one stabilizing agent may be added to the composition in order to help maintain the crystals in the desired size range in the liquid solution.

Typically, the stabilizing agent is a polymer which may be used alone or in combination with one or more other stabilizing agents, such as surfactants, to stabilize the individual crystals by inhibiting and/or preventing, for at least a period of time, the formation of larger crystals, e.g., through agglomeration, ripening (e.g. Ostwald ripening), and/or recrystallization. In certain embodiments, the polymer can be a polymer that comprises charged moieties. In other embodiments, the polymer may be neutral. Sometimes, one or more surfactants may be employed as stabilizing agents, either alone or together with a polymer. Various polymers and/or surface-active molecules can have an affinity for the oltipraz crystal surface, e.g., such that they can coat, adsorb, adhere or otherwise associate with all or a portion of the crystals and thereby interfere with the crystals agglomerating, ripening, and/or recrystallizing to form larger crystals.

As noted above, the quantity of stabilized oltipraz crystals in the liquid suspension then may be further treated to produce a dry composition, e.g., by mixing a bulking agent with a liquid composition of crystals and then removing the liquid from the composition to form a dry composition, e.g., by spray-drying or lyophilizing an aqueous composition. The bulking agent can also serve as a stabilizing agent, either alone or in combination with other stabilizing agents. When a bulking agent is used, the dry composition thus will comprise both the crystalline oltipraz drug and the bulking agent, as well as any other stabilizing agents or other ingredients that are present in the liquid composition prior to the removal of the water and/or other liquid solvent. When the dry composition is then mixed with liquid (e.g., water), the stabilized oltipraz crystals and other ingredients present in the dry composition will then be released into the liquid.

The term "dry composition" as used herein refers to a composition that substantially excludes water or other solvent. As used in this disclosure, the term "substantially" is intended to encompass both "wholly" and "largely but not wholly." Thus, a dry composition that substantially excludes water is a composition that wholly excludes water (and/or other solvent) or largely excludes water (and/or other solvent). That is, the dry composition either has no water or solvent, or at most only a small or residual amount of water or solvent such that the composition is not moist or wet.

1. Liquid Compositions Comprising Stabilized Oltipraz Crystals in Suspension

Any suitable method can be used to produce the formulated oltipraz compositions of this Section A. Suitable methods are described in the '1312 PCT, the disclosure of which is expressly incorporated herein by reference to include all such formulated oltipraz compositions and methods of making them. Recrystallized oltipraz such as produced by U.S. Pat. No. 4,110,450 or Framroze PCT/IN2016/050197 can be wet milled in the presence of at least one stabilizing agent that can help to stabilize the drug crystals to reduce or prevent the growth of crystals by agglomeration, ripening and/or recrystallization. The wet milling of oltipraz crystals in the presence of the stabilizing agent thus creates a liquid (e.g., aqueous) composition comprising the stabilized oltipraz crystals in suspension in the composition. Combinations of stabilizing agents may be added to the wet milling composition to facilitate stabilization of the crystals.

As an alternative to wet-milling, oltipraz crystals useful for compositions of this Section A may be made by other methods of producing nanocrystals, e.g., by antisolvent precipitation, supercritical fluid precipitation, printing techniques adapted from the semiconductor industry, or three-dimensional printing or other known means of producing nanoparticles.

For example, a liquid composition comprising at least a portion of the stabilized oltipraz crystals as described in this Section A and optionally other additives (the crystals having been prepared, e.g., from a wet milling or antisolvent process), can be admixed with a bulking agent to form a liquid composition comprising the bulking agent and crystals in suspension. In certain embodiments, a liquid composition comprising at least a portion of the crystals and other additives, e.g., from a wet milling or antisolvent process, is then admixed with a bulking agent to form a liquid composition comprising the bulking agent and crystals in suspension. That liquid composition then may be processed to remove the liquid, e.g., by spray-drying or lyophilization in the case of aqueous solutions, and subject to additional drying if necessary, to form a dry composition that substantially excludes water. Other processes known to persons skilled in the art also may be used to prepare dry compositions comprising the stabilized oltipraz crystals. For example, the liquid composition can be sprayed onto sugar spheres or beads for drying. When dry, the sugar spheres or beads become a dissolvable carrier for the drug and other additives, e.g., the stabilizing agent(s) and/or bulking agent(s). The dry composition thus comprises the stabilized oltipraz crystals and any ingredients other than the liquid solvent (e.g., water) that were present in the liquid composition. The dry composition can be then later admixed with a liquid comprising water, at which time the bulking agent can facilitate release of the stabilized oltipraz crystals to again form an aqueous composition comprising such stabilized crystals in suspension. Any additional nonvolatile ingredients present in the liquid composition prior to removal of water or other solvent will be carried along in the dry composition and also released into the re-suspended aqueous composition.

Depending on the amount of water and/or other liquid solvent used in the milling or other nanocrystal production process such as antisolvent precipitation, the oltipraz crystals can be present in an amount ranging from 2% or less to 40% or more by weight of the liquid composition prior to the addition of any bulking agent. Within that range are included the following ranges in percent by weight of 1 to 20%, 2 to 5%, 5 to 10%, 10 to 15%, 10 to 20%, 15 to 20%, 15 to 25%, 15 to 30%, 20 to 30%, 25 to 35%, 30 to 40%, or more than 40%. In some embodiments, the crystals can be between 6 and 11% by weight of the liquid composition, e.g., between 7 and 10%. In certain such embodiments, the concentration of the crystals in the liquid is about 1% to about 30% by weight, about 4% to about 15% by weight, about 5% to about 10% by weight, about 6% to about 10% by weight, about 6% to about 12% by weight, about 7% to about 10% by weight, about 8% to about 10% by weight, or about 8.6% by weight of the suspension. Accordingly, the liquid composition typically comprises between about 1 to about 40 wt %, such as from about 2 to about 20 wt %, e.g. from about 4 to about 15 wt %, typically from about 6 to about 12 wt % such as from about 7 to about 10 wt %, e.g. about 8 to about 9 wt % such as about 8.6 wt % of oltipraz crystals, based on the weight of the liquid composition prior to the addition of any bulking agent.

Alternatively, the amount of crystals can be calculated as a percent of the components other than the water or other liquid solvent in the composition prior to addition of a bulking agent. As a percent of the non-solvent components, the crystals can be present in an amount ranging from less than 10% up to more than 60% by weight of the non-solvent components prior to the addition of any bulking agent. Within that range are included the following ranges in percent by weight of 1 to 5%, 5 to 10%, 10 to 15%, 15 to 20%, 20 to 30%, 25 to 40%, 30 to 40%, 40 to 50%, 50 to 60%, 60 to 70%, and over 70%. In certain embodiments, the crystals comprise between 30 and 70%, e.g., between 50 and 65%, or between 55 and 60%, or about 57% by weight of the non-solvent components prior to addition of any bulking agent. Accordingly, the non-solvent components in the composition typically comprise from about 1 to about 70 wt % oltipraz crystals based on the overall weight of the non-solvent components in the composition; more typically the non-solvent components comprise from about 30 to about 65 wt % such as from about 50 to about 60 wt %, e.g. from about 55 to about 58 wt %, such as about 57 wt % of the composition based on the overall weight of the non-solvent components in the composition.

Once a bulking agent is added, the percentage by weight of the stabilized oltipraz crystals typically will decrease. Within the liquid composition before removal of water or other liquid solvent but after addition of the bulking agent, the crystals may comprise from 1% up to 10% or more of the liquid composition. Within such ranges are, e.g., 1 to 2%, 1 to 3%, 2 to 3%, 2 to 4%, 2 to 5%, 2 to 6%, 3 to 5%, 3 to 6%, 3 to 7%, 4 to 7%, 4 to 8%, 5 to 9% and 6 to 10%. In some embodiments, the crystals can comprise between 2 and 6% of the liquid suspension comprising the bulking agent, e.g., between 3 and 5%, or about 4%. In certain such embodiments, the concentration of the crystals in the liquid is about 0.1% to about 4% by weight, about 0.2% to about 3.5% by weight, about 0.5% to about 3.5% by weight, about 1% to about 3.5% by weight, about 1.5% to about 3% by weight, about 2% to about 3% by weight, or about 2.5% by weight of the formulation. Accordingly, the concentration of oltipraz crystals in the liquid is typically from about 0.1 to about 10 wt % (based on the weight of the liquid composition before removal of water or other liquid solvent but after addition of a bulking agent if present), more often from about 0.5 to about 8 wt %, e.g. from about 1 to about 6 wt %, such as from about 2 wt % to about 5 wt %, such as from about 2.5 wt % to about 4 wt %.

Alternatively, the amount of the crystals can be calculated as a percent of the non-solvent (e.g., non-water) components following addition of a bulking agent. This percentage of oltipraz in the non-solvent components also may be referred to as the "drug loading" percentage because it represents the amount of the stabilized oltipraz crystals in the dry composition. As a percent of the non-solvent components, i.e., the solids, the stabilized oltipraz crystals can be present in an amount ranging from less than 2% up to 25% or more. Within that range are included the following ranges in percent by weight of 0.5 to 1%, 1% to 2%, 2 to 4%, 3 to 5%, 4 to 7%, 5 to 8%, 5 to 10%, 6 to 8%, 6 to 9%, 6 to 10%, 7 to 11%, 7 to 12%, 8 to 12%, 8 to 13%, 9 to 13%, 9 to 14%, 10 to 15%, 11 to 16%, 12 to 17%, 13 to 18%, 14 to 19%, 15 to 20% and 20 to 25%. Accordingly, the stabilized oltipraz crystals are typically from about 0.5 to about 25 wt % (based on the weight of the non-solvent components after addition of a bulking agent if present), more often from about 1 to about 25 wt %, such as from about 5 to about 20 wt %, e.g. from about 6 to about 19 wt %, such as from about 10 to about 18 wt %, e.g. about 15 to about 17 wt %, such as about 16 wt % (e.g. about 16.7 wt %). The crystals can comprise between about 5% and about 10% by weight of the non-solvent components, e.g., between about 6% and about 9%, such as about 7%. For example, in certain embodiments the crystals can comprise between 5 and 10% by weight of the non-solvent components, e.g., between 6 and 9%, or about 7%. In other embodiments the crystals comprise between 10 and 20% by weight of the powder, e.g., between 13 and 17%, e.g., about 15% by weight of the non-solvent components.

In some embodiments of the formulated oltipraz compositions of this Section A, a dry composition comprising an oltipraz drug loading of about 15% will provide good results when reconstituted with water, i.e., the dry composition quickly forms a dispersion (e.g., less than a minute) with moderate or gentle shaking, with the crystals substantially retaining their MHD from prior to drying. Typically, a dry composition comprising an oltipraz drug loading of about 20% or higher provides less desirable results when reconstituted with water, i.e., the dry composition slowly forms a dispersion (e.g., several minutes) with moderate or vigorous shaking, and the dispersion may comprise larger particles, e.g., up to 2 microns in size. In such cases, it is advantageous to reduce the oltipraz drug loading to a lower level that provides the desired characteristics in terms of rapidly forming a dispersion of crystals that retain their original MHD. Without being bound by any particular theory, it is believed that, as the concentration of oltipraz crystals within the dry composition approaches 20%, there is less of the other ingredients in the composition (e.g., stabilizing agents and/or bulking agents) to separate the individual crystals, which in turn leads to more interactions between the crystals, resulting in slower formation of a dispersion in an aqueous or other solvent environment and also the formation of larger particles, e.g., by agglomeration. Hence, compositions of this Section A comprising oltipraz drug loadings of 12 to 20% are contemplated, including loadings of 12 to 13%, 12 to 14%, 12 to 15%, 13 to 14%, 13 to 15%, 13 to 16%, 14 to 15%, 14 to 16%, 14 to 17% 15 to 16%, 15 to 17%, 15 to 18%, 16 to 17%, 16 to 18%, 16 to 19%, 17 to 18%, 17 to 19%, 17 to 20%, 18 to 19%, and 18 to 20%, including drug loadings of about 12%, about 13%, about 14%, about 15%, about 16%, about 17%, about 18%, about 19% and about 20% are all contemplated. Accordingly, the dry composition typically has an oltipraz drug loading of about 12 to about 20 wt % such as from about 14 to about 18 wt %, e.g. from about 15 to about 17 wt %, such as about 16 or about 16.7 wt %.

A. Stabilizing Agents

As mentioned above, liquid compositions comprising the stabilized oltipraz crystals of this Section A typically also comprise one or more stabilizing agents to stabilize the oltipraz crystals. In some circumstances, in the absence of at least one stabilizing agent (or a combination of agents that together act to stabilize), over time oltipraz crystals in liquid suspension can agglomerate, ripen, and/or recrystallize to form larger crystals. It is typically desirable to maintain the crystals in the size range that results from the wet milling, antisolvent precipitation or other crystal-production processes for a period of time, e.g., to permit storage of the materials prior to the next step in processing, or to allow testing or validation of crystal size or some other feature of a batch of oltipraz crystals. In such instances, at least one stabilizing agent may be provided to the liquid composition of crystals, e.g., during and/or after milling, or during and/or after antisolvent precipitation, in order to stabilize the crystals to thereby prevent and/or inhibit the milled crystals from agglomerating, recrystallizing and/or ripening to form larger crystals. Thus, any agent that either alone or in combination with another agent serves to stabilize the crystals to thereby prevent and/or inhibit the milled crystals from agglomerating, recrystallizing and/or ripening to form larger crystals, is deemed a stabilizing agent. If a combination of two or more agents is used to stabilize crystals, then each of the two or more co-stabilizers is deemed to be a stabilizing agent even though an individual agent within the combination may be unable to stabilize the crystals by itself, or unable to stabilize the crystals by itself for the desired length of time.

Alternatively, if the stabilized oltipraz crystals of this Section A are to be quickly converted to a dry form, e.g., by mixing with a bulking agent and being spray-dried or lyophilized, a stabilizing agent may be unnecessary. This may be an acceptable alternative if the intended method of administration does not require the stabilized oltipraz crystals to later have stability upon resuspension in water, e.g., if the resuspension will occur immediately before administration of the dry composition, e.g., in pill or tablet form. Alternatively, a single agent such as copovidone or PVP-VA64 (polyvinylpyrrolidone vinyl acetate, a copolymer of 1-vinyl-2-pyrrolidone and vinyl acetate in a ratio of 6:4 by mass, commercially available e.g. from BASF as Product No. 95405-2-43) may be able to serve both as a stabilizing agent and as a bulking agent, thereby rendering additional stabilizing agents unnecessary and providing a composition that will exhibit stability upon resuspension in water and/or other liquid.

Generally speaking, stabilizing agents are surface active agents that affect the surface of the crystals in some way. While not wishing to be bound to a particular theory by which a stabilizing agent can operate to stabilize the crystals, it is believed that the stabilization typically can take one of two forms. Steric stabilization can be accomplished by mixing the crystals with either an amphiphilic or water-soluble material that interacts with the crystal surface, which keeps crystal faces from interacting by providing a barrier between crystals. This is typically accomplished by addition of polymer, surfactant, or both. Alternatively, electrostatic stabilization can be accomplished by modifying the crystal surface with a charge through addition of a charged compound (polymer, surfactant, or other interacting charged molecule or ion). Because all or at least many of the crystals then carry the same charge, in theory they repel each other, thereby increasing the energy barrier required for two crystal faces to get close enough to fuse together.

Typically, the stabilizing agent maintains the size of the crystals in the liquid composition within a specified size range for a period of time following wet milling. Such a period can be on the order of hours, e.g., at least 1 hour, at least 6 hours, at least 12 hours, at least 24 hours, at least two days, at least three days, at least a week, at least two weeks, at least a month, at least two months, and at least six months, or longer.

Typically, the stabilizing agent comprises a polymer that is either neutral or capable of associating charged moieties with the individual milled oltipraz crystals, e.g., by coating the crystals, or adsorbing or otherwise associating with them. Such polymers thus may be neutral or may include moieties that provide either a positive or negative charge to the polymer, and in that way the charged moieties associated with the crystals may be able to repel other crystals having like charges on their surfaces. Nonionic, cationic or anionic polymers may be used as stabilizing agents, including especially pharmaceutically acceptable nonionic, cationic and anionic polymers. Combinations of such polymers also may be employed. Sometimes, the stabilizing agent may comprise a carbohydrate and/or protein, e.g., albumin.

The polymer may be an acrylate polymer comprised of a plurality of repeat units derived from identical or different monomers. Acrylate polymers comprising different types of repeat units are referred to herein as "copolymers". Exemplary repeat units of acrylate polymers include repeat units derived from methacrylate, alkyl acrylate (such as methyl acrylate or ethyl acrylate), hydroxyethyl methacrylate, ethylacrylate, butyl methacrylate, acrylonitrile, or alkyl cyanoacrylates. Typically, when the carboxylic acid functionality of acrylate is not protected as an ester, the acid can exist as a protonated carboxylic acid (—COOH) or as an anionic salt (e.g., —COONa).

The polymer also may be an acrylate- and alkenyl ether-based co-polymer (e.g., Carbopol® type polymers such as Carbopol 974P NF), polyvinylpyrrolidine (e.g., PVP K15 or K30), a cellulosic polymer such as a cationic hydroxyethyl cellulose (e.g., in the Polymer JR family), hydroxypropylcellulose (HPC e.g. HPC EF typically having a molecular weight of about 80 kDa), hydroxypropyl methylcellulose (HPMC e.g. HMPC E3 typically having viscosity of about 3 cP at 2% in water), or hydroxypropyl methylcellulose acetate succinate (HPMCAS). The polymer also may be a copovidone (e.g., PVP-VA64), poly(ethylene oxide), or a poloxamer (e.g., a poly(propylene oxide) and poly(ethylene oxide) copolymer). The polymer also may be an acrylamide polymer. For example, the polymer may be comprised of repeat units derived from acrylamide.

The repeat units can be functionalized by adding groups that can change the permeability, hydrophobicity, or other properties of the formulation. For example, certain repeat units can be functionalized by tertiary amines or by quaternary amines, such as quaternary trialkylammonium substituents.

An acrylate polymer may be comprised of repeat units derived from a methacrylate monomer. In certain embodiments, the acrylate polymer comprises repeat units derived from an acrylate monomer and repeat units derived from a methacrylate monomer. Typically, the acrylate polymer comprises repeat units derived from ethyl acrylate and repeat units derived from methyl methacrylate. Typically, some of the ethyl acrylate monomeric units are functionalized on the ethyl group by a trimethylammonium chloride group. The acrylate polymer of the crystal may be poly(ethyl acrylate-co-methyl methacrylate-co-trimethylammonioethyl methacrylate chloride) 1:2:0.2. Poly(ethyl acrylate-co-methyl methacrylate-co-trimethylammonioethyl methacrylate chloride) 1:2:0.2 may be sold as EUDRAGIT® RL Other polymethacrylate-based copolymers in the Eudragit family may be used, e.g., Eudragit S, L, E or RS.

Typically, the polymer is one or more of an acrylate- and alkenyl ether-based co-polymer, polyvinylpyrrolidone, hydroxypropylcellulose, hydroxypropyl methylcellulose, a copovidone such as PVP-VA64, and a polymethacrylate-based copolymer such as EUDRAGIT® RL. More often, the polymer is one or more of a copovidone such as PVP-VA64 and a polymethacrylate-based copolymer such as EUDRAGIT® RL.

Alternatively, or in addition to the above polymers, other surface-active ingredients may be added to the liquid compositions that comprise the crystals for the purpose of helping to stabilize the crystals in suspension. In addition to helping stabilize the crystals, such surfactants also may aid in the dispersion of crystals and/or other ingredients in a particular liquid composition. Indeed, such surfactants may be added solely for the purpose of aiding in the dispersion of crystals and/or other ingredients in the liquid compositions described herein that are prepared from the dry compositions described herein.

Surfactants suitable for use in the compositions described herein may be ionic or non-ionic. These include, but are not limited to: sodium isostearate, cetyl alcohol, polysorbates (Polysorbate 20, Polysorbate 40, Polysorbate 60, Polysorbate 80), steareth-10 (Brij 76), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol, N,N-dimethyldodecylamine-N-oxide, hexadecyltrimethylammonium bromide (HTAB), polyoxyl 10 lauryl ether, bile salts (such as sodium deoxycholate or sodium cholate), polyoxyl castor oil, nonylphenol ethoxylate, cyclodextrins, lecithin, dimethicone copolyol, lauramide DEA, cocamide DEA, cocamide MEA, oleyl betaine, cocamidopropyl betaine, cocamidopropyl phosphatidyl PG-dimonium chloride, dicetyl phosphate (dihexadecyl phosphate), ceteareth-10 phosphate, methylbenzethonium chloride, dicetyl phosphate, ceteth-10 phosphate (ceteth-10 is the polyethylene glycol ether of cetyl alcohol where n has an average value of 10; ceteth-10 phosphate is a mixture of phosphoric acid esters of ceteth-10), ceteth-20, Brij S10 (polyethylene glycol octadecyl ether, average $M_n$~711), PEG-20 phytosterol, and Poloxamers (including, but not limited to, Poloxamer 188 $(HO(C_2H_4O)_a(CH(CH_3)CH_2O)_b(C_2H_4O)_aH$, average molecular weight 8400) and Poloxamer 407 $(HO(C_2H_4O)_a(CH(CH_3)CH_2O)_b(C_2H_4O)_aH$, wherein a is about 101 and b is about 56)). Poloxamers are nonionic triblock copolymers composed of a central hydrophobic chain of polyoxypropylene (poly(propylene oxide)) flanked by two hydrophilic chains of polyoxyethylene (poly(ethylene oxide)). Poloxamer surfactants, also sold under the trade name of Pluronic surfactants, thus may be employed, e.g., Pluronic F-68, which also is known as Poloxamer 188. The surfactants that may be used in the formulation may be non-ionic surfactants such as polyoxyethylene glycol alkyl ethers (e.g., octaethylene glycol monododecyl ether, pentaethylene glycol monododecyl ether, and polyethylene glycol alkyl ethers such as Brij® Detergents), polyoxypropylene glycol alkyl ethers, glucoside alkyl ethers (e.g., decyl glucoside, lauryl glucoside, or octyl glucoside), polyoxyethylene glycol alkylphenol ethers (e.g. Triton X-100, Nonoxyol-9), glycerol alkyl esters, polyoxyethylene glycol sorbitan alkyl esters (e.g., polysorbates), sorbitan alkyl esters, cocamides, and Poloxamers (mentioned above). In certain embodiments, the non-ionic surfactant may be polyoxyethylene (20) sorbitan monooleate (polysorbate 80). Polysorbate 80 is available under the tradename Tween 80.

Typically, the surfactant is one or more of poloxamers such as Pluronic F-68 (i.e., Poloxamer 188), polysorbates such as polysorbate 80 (Tween 80), povidone-based polymers, lecithin, PEG-castor oil derivatives, TPGS, bile acids, tyloxapol, acacia, and sodium lauryl sulfate. More typically, the surfactant is polysorbate 80 (Tween 80).

As described in more detail below, appropriate combinations or mixtures of surfactants such as those above may also be used, either with or without other stabilizing agents such as the polymers described above. For example, in certain embodiments the stabilizing agents can comprise a combination of a neutral polymer and a neutral surfactant, a cationic polymer and a neutral surfactant, or a neutral polymer and an anionic surfactant. As noted above, however, such stabilizing agents may be unnecessary when the bulking agent also acts as a stabilizing agent or when no stabilizing agent is desired.

When such stabilizing agents are employed, depending on the amount of water and/or other solvent used in the milling process, the stabilizing agent(s) can be present in an amount ranging from less than 1 percent to 25% or more by weight of the liquid composition of this Section A prior to the addition of any bulking agent. Within that range are included the following ranges in percent by weight of 0.1 to 1%, 1 to 3%, 3 to 7%, 5 to 10%, 5 to 15%, 5 to 20%, 10 to 15%, 10 to 20%, 10 to 25%, 15 to 20%, 15 to 25%, 7.5 to 25%, or more than 25%. In some embodiments, the stabilizing agent(s) can comprise between 2 and 10%, e.g., between 4 and 8% or about 6.4%. Accordingly, the amount of stabilizing agent(s) in the liquid composition of this Section A prior to addition of any bulking agent is typically from about 0.1 to about 25 wt %, such as from about 1 to about 20 wt %, such as from about 2 to about 10 wt %, e.g. from about 4 to about 8 wt %, such as from about 5 to about 7 wt %, e.g. about 6 wt %, such as about 6.4 wt %.

Alternatively, the amount of stabilizing agent can be calculated as a percent of the non-solvent components prior to addition of a bulking agent. As a percent of the non-solvent components, the stabilizing agent can be present in an amount ranging from 10 percent or less to 75% or more by weight of the non-liquid components prior to the addition of any bulking agent. Within that range are included the following ranges in percent by weight of 0.1 to 10%, 10 to 20%, 20 to 30%, 30 to 40%, 40 to 50%, 50 to 60%, 60 to 75% or more. In some embodiments, the stabilizing agent can be between 30 and 55% by weight of the non-solvent components, e.g., between 35 and 50%, or between 40 and 45%, or about 42.7%. Accordingly, the amount of stabilizing agent(s) in the composition prior to addition of any bulking agent is typically from about 1 to about 75 wt %, such as from about 10 to about 60 wt %, such as from about 20 to about 55 wt %, e.g. from about 30 to about 50 wt %, such as from about 40 to about 45 wt %, e.g. about 42 wt %, such as about 42.7 wt %, based on the weight of non-solvent components.

Once a bulking agent is added, the percentage by weight of the stabilizing agent(s) typically will decrease. Within the liquid composition before removal of water and/or other liquid solvent, following addition of a bulking agent, the stabilizing agent(s) may comprise from less than 1% up to 30% or more of the liquid composition, again depending on the amount of water or other solvent in the composition prior to a water removal step. Within such ranges are, e.g., 0.5 to 1%, 1 to 2%, 1 to 3%, 2 to 3%, 2 to 4%, 2 to 5%, 3 to 6%, 3 to 7%, 4 to 7%, 4 to 8%, 5 to 9%, 6 to 10%, 10 to 15%, 15 to 20%, 20 to 25%, 25 to 30% and more than 30%. In some embodiments, the stabilizing agent(s) can comprise between 1 and 5% by weight of the liquid suspension comprising the bulking agent, e.g., about 2 to 4%, or about 3.1%. Accordingly, the amount of stabilizing agent(s) in the liquid composition (based on the weight of the liquid composition before removal of water or other liquid solvent but after addition of a bulking agent if present) is typically from about 0.1 to about 30 wt %, such as from about 1 to about 10 wt %, such as from about 2 to about 5 wt %, e.g. from about 3 to about 4 wt %, such as about 3.1 wt %.

Alternatively, the amount of stabilizing agent(s) can be calculated as a percent of the non-solvent components following addition of a bulking agent. As a percent of the non-liquid components, the stabilizing agent(s) can be present in an amount ranging from less than 2% up to 20% or more. Within that range are included the following ranges in percent by weight of 2 to 4%, 3 to 5%, 4 to 7%, 5 to 8%, 5 to 10%, 6 to 8%, 6 to 9%, 6 to 10%, 7 to 11%, 7 to 12%, 8 to 12%, 8 to 13%, 9 to 13%, 9 to 14%, 10 to 15%, 11 to 16%, 12 to 17%, 13 to 18%, 14 to 19% 15 to 20%, and more than 20%. For example, in certain embodiments the stabilizing agent can comprise between 5 and 15% by weight of the non-solvent components, e.g., between 9 and 13%, or about 11.2%. Such amounts will also correspond to the amounts of the stabilizing agent in the dry composition. Accordingly, the amount of stabilizing agent(s) in the composition (based on the weight of non-solvent components after addition of a bulking agent if present) is typically from about 2 to about 20 wt %, such as from about 4 to about 17 wt % such as from about 8 to about 15 wt %, e.g. from about 10 to about 12 wt %, such as about 11 wt %, e.g. about 11.2 wt %.

b. Combinations of Stabilizing Agents

As noted above, combinations of stabilizing agents may be employed to assist in stabilizing the crystals in a liquid composition comprising oltipraz crystals as described in this Section A and/or assist in dispersing the crystals from a dry composition comprising oltipraz crystals as described in this Section A. For example, as noted above, in certain embodiments, nonionic surfactants may be combined with a cationic polymer or an anionic polymer. In other embodiments, an ionic surfactant (anionic or cationic) is combined with a neutral polymer. Other embodiments can combine a neutral polymer and nonionic surfactant.

Some exemplary combinations include, with or without an anti-foaming agent such as simethicone, (i) Eudragit RL in combination with Tween 80, Pluronic F-68 and/or sodium lauryl sulfate, (ii) Carbopol 974P NF RL in combination with Tween 80, Pluronic F-68 and/or sodium lauryl sulfate, (iii) PVP (K15 or K30) RL in combination with Tween 80, Pluronic F-68 and/or sodium lauryl sulfate, (iv) HPC EF RL in combination with Tween 80, Pluronic F-68 and/or sodium lauryl sulfate, and (v) HPMC E3 RL in combination with Tween 80, Pluronic F-68 and/or sodium lauryl sulfate. Some examples of such combinations are illustrated in Table 1 below.

TABLE 1

| Components | | Formulation Composition (mg/mL) | | | | | |
|---|---|---|---|---|---|---|---|
| Function | Name | 1 | 2 | 3 | 4 | 5 | 6 |
| API | Oltipraz | 50 | 50 | 50 | 50 | 50 | 50 |
| Stabilizing Agent (Polymer) | Eudragit RL | 25 | | | | | |
| | Carbopol 974P NF | | 5* | | | | |
| | PVP (K15 or K-30) | | | 25 | | | |
| | HPC EF | | | | 25 | | 25 |
| | HPMC E3 | | | | | 25 | |
| Stabilizing Agent (Surfactant) | Tween 80 | 12.5 | | | 12.5 | | |
| | Pluronic F68 | | 12.5 | 12.5 | | 12.5 | |
| | SLS | | | | | | 12.5 |
| Anti-foam | Simethicone | 0.5 | 0.5 | 0.5 | 0.5 | 0.5 | 0.5 |

*Added after milling

Among the various combinations, Eudragit RL in combination with Tween 80 or HPC EF in combination with Tween 80 have been found to provide acceptable results and typically to be particularly beneficial in terms of forming and keeping small crystals stable for a period of time. As discussed below, other combinations of the foregoing polymers and surfactants may be suitable depending on the particular composition and method of administration. The amounts of the individual components in such combinations are as set forth above for the individual components.

c. Other Surface-Active Agents

As noted above, surface active agents, including those listed above, may be added to the liquid compositions described in this Section A for purposes other than stabilizing oltipraz crystals, e.g., to aid in the dispersion of crystals upon resuspension with water and/or other liquid, or to serve other purposes beyond stabilizing the crystals, e.g., emulsifiers and anti-foam agents. For example, such ingredients can be added for the purpose of improving processes and/or compositions such as the processes for making the crystals or the properties of the composition comprising crystals.

In certain embodiments, e.g., an emulsifier may be added. Suitable emulsifiers include, but are not limited to, *Glycine soja* protein, sodium lauroyl lactylate, polyglyceryl-4 diisostearate-polyhydroxystearate-sebacate, behentrimonium methosulfate-cetearyl alcohol, non-ionic emulsifiers like emulsifying wax, polyoxyethylene oleyl ether, PEG-40 stearate, carbomer, cetostearyl alcohol (cetearyl alcohol), ceteareth-12, ceteareth-20, ceteareth-25, ceteareth-30, ceteareth alcohol, Ceteth-20 (Ceteth-20 is the polyethylene glycol ether of cetyl alcohol where n has an average value of 20), oleic acid, oleyl alcohol, glyceryl stearate, PEG-75 stearate, PEG-100 stearate, and PEG-100 stearate, ceramide 2, ceramide 3, stearic acid, cholesterol, laureth-12, steareth-2, and steareth-20, or combinations/mixtures thereof, as well as cationic emulsifiers like stearamidopropyl dimethylamine and behentrimonium methosulfate, or combinations/mixtures thereof.

In certain embodiments, an anti-foam agent may be added. Anti-foam agents may be used to reduce the formation of foam, e.g., in the process of making the crystals. Anti-foam agents that may be used include, but are not limited to, oil-based anti-foam agents [e.g., a hydrophobic silica or a wax (e.g., paraffin, ester waxes, fatty alcohol waxes, ethylene bis(stearamide)) in mineral or vegetable oil], powder defoamers, water-based defoamers (e.g., long chain fatty alcohols, fatty acid soaps, or esters in a white oil or vegetable oil), silicone-based defoamers [hydrophobic silica in silicone oil], polyethylene glycol- or polypropylene glycol-based defoamers, or alkyl polyacrylates. In certain preferred embodiments, the anti-foam agent is a silicone-based anti-foam agent. In certain embodiments, the anti-foam agent is poly(dimethylsiloxane), or silicon dioxide (simethicone).

Depending on the amount of water and/or other liquid used in the milling process, prior to the addition of a bulking agent, such additional surface-active ingredient(s) can be present in cumulative amounts ranging from less than 1 to more than 10% by weight of the liquid suspension. Within that range are included the following ranges in percent by weight, 0.1 to 1%, 1 to 3%, 1 to 4%, 1 to 5%, 2 to 5%, 2 to 6%, 3 to 6%, 3 to 7%, 4 to 7%, 4 to 8%, 5 to 8%, 5 to 9%, and 6 to 10%, and greater than 10%. For example, an anti-foam agent can be in an amount from about 0.01% to about 2% by weight of the liquid composition comprising the crystals, e.g. from about 0.01% to about 2%, from about 0.05% to about 1.5%, from about 0.1% to about 1%, from about 0.3% to about 0.9%, or from about 0.4% to about 0.8% by weight of the crystal. Typically, an anti-foam agent can be present in an amount from about 0.01% to about 2% by weight of the solid components (excluding bulking agents if present) in the liquid composition comprising the crystals, e.g. from about 0.01% to about 2%, such as from about 0.05% to about 1.5%, e.g. from about 0.1% to about 1%, such as from about 0.3% to about 0.9%, e.g. from about 0.4% to about 0.8% by weight of the crystal.

For example, a composition comprising oltipraz crystals of this Section A may typically comprise a combination of solubilizing agents selected from (i) one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and (ii) one or more of sodium lauryl sulfate, a poloxamer such as Pluronic F-68 and polysorbate 80. Another surface-active ingredient may also be present such as an emulsifiers and/or an anti-foam agent. More typically the composition may comprise (i) one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; (ii) one or more of sodium lauryl sulfate, a poloxamer such as Pluronic F-68 and polysorbate 80; and optionally (iii) an antifoam agent such as poly(dimethylsiloxane) or silicon dioxide (simethicone). Still more typically the composition may comprise (i) one or more of a copovidone such as PVP-VA64 and a polymethacrylate-based copolymer such as EUDRAGIT® RL; (ii) polysorbate 80 (Tween 80); and optionally (iii) simethicone. In such compositions, the amount of component (i) is typically from about 5 to about 40 wt %, preferably from about 20 to about 35 wt % such as from about 25 to about 30 wt % based on the weight of solid components (excluding bulking agents) in the composition. The amount of component (ii) is typically from about 10 to about 20 wt %, preferably from about 12 to about 18 wt % such as from about 14 to about 15 wt % based on the weight of solid components (excluding bulking agents) in the composition. If present, the amount of component (iii) is typically from about 0.1 to about 1 wt %, preferably from about 0.3 to about 0.8 wt % such as from about 0.5 to about 0.7 wt % based on the weight of solid components (excluding bulking agents) in the composition.

d. Other Components

The liquid compositions described in this Section A also can comprise liquids in addition to water. For example, the liquid may be an aqueous buffer solution. Pharmaceutically acceptable buffers include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, and tris(hydroxymethyl)-aminomethane or mixtures thereof. Alternatively, the compositions described herein as aqueous compositions may be instead prepared in a liquid solvent other than one that contains water, e.g., a polar organic solvent, such as methanol and/or ethanol. If liquids other than water are used, then advantageously, the liquid is one in which oltipraz is not more than minimally soluble, e.g., not more than 0.35%, 0.1%, 0.05%, 0.01%, 0.005%, 0.001%, or 0.0008% by weight solvated oltipraz in solvent. Typically, therefore, if liquids other than water are used, then advantageously, the liquid is one in which oltipraz is not more than minimally soluble, e.g., the liquid does not support more than 0.35%, e.g., not more than 0.1%, such as not more than 0.05%, e.g. not more than 0.01%, such as not more than 0.005%, e.g. not more than 0.001% or 0.0008% by weight solvated oltipraz in solvent. Combinations of liquids also may be used, including combinations of water and other liquids such as one or more polar organic solvents. Hence, although it is contemplated that aqueous compositions comprising oltipraz crystals as described in this Section A can be used throughout this disclosure, it is also contemplated that the water component in any of such aqueous compositions could be replaced in whole or in part by a liquid other than water. Where a solvent other than or in addition to water is used, the percentages given above for the stabilizing agents and other ingredients typically remain the same or substantially the same.

Liquid compositions comprising oltipraz crystals as described in this Section A, e.g., aqueous or otherwise, may be useful for milling. Other liquid compositions comprising oltipraz crystals as described in this Section A may be useful for spray-drying or lyophilization-based methods of generating the crystals in a dry composition. The total concentration of ingredients in such liquid formulations may be represented by the percentage by weight of combined solids in the formulation, wherein the combined solids are the non-solvent components, e.g., the crystals and any additives such as a stabilizing agent, surfactant, and/or a bulking agent that remain once the solvent is removed. The appropriate level of solids in a liquid composition as described in this Section A can vary depending on the use of the composition. For example, the total solids in a composition that is undergoing wet milling may be higher or lower than the total solids in a composition that also comprises a bulking agent and is undergoing a process in which liquid is being removed, e.g., spray-drying or lyophilization. In certain embodiments, for example including compositions for milling and/or spray-drying or lyophilization, the concentration of the solids in the liquid described herein can be about 5% to about 35% or more by weight, including ranges of from 5 to 10%, 10 to 15%, 10% to 20%, 15 to 20%, 15 to 25%, 20 to 25%, 20 to 30%, 25 to 30%, 25 to 35%, or more than 35%. In some embodiments, the total solids can be about 12% to about 18% by weight, about 13% to about 18% by weight, about 14% to about 17% by weight, or about 16% by weight of the formulation. Typically, therefore, the total solids can be from about 12% to about 18% by weight, e.g. from about 13% to about 18% by weight, such as from about 14% to about 17% by weight, e.g. about 16% by weight of the formulation. Typically, in some liquid compositions for milling, the total solids can be from about 20 to 30% by weight, e.g., from about 22 to about 27% by weight, such as about 25% by weight. In some embodiments, e.g., in some liquid compositions for milling, the total solids can be from about 20 to 30% by weight, e.g., about 22 to 27% by weight, about 25% by weight. In some embodiments, e.g., spray-drying compositions, the total solids can be from about 25 to 30% by weight, e.g., about 28% by weight. Using the guidance provided herein, one of ordinary skill will be able to determine an acceptable level of solids for compositions described in this Section A.

e. Crystal Sizes and Distribution, Such as Crystal Sizes and Distribution in Liquid Suspensions Due to the inherent variability of the wet milling or other crystal-forming process such as antisolvent precipitation described in this Section A, the individual stabilized crystals of oltipraz formed from such processes will typically vary in size, and thus a quantity of oltipraz crystals produced by such processes can typically be characterized by a distribution of crystals of varying sizes. When in an aqueous suspension, the quantity of stabilized crystals described herein generally will have a MHD of between 30 and 2000 nm. Generally speaking, larger crystals will tend to settle faster in aqueous compositions, and so quantities of smaller crystals, e.g., those having an MHD from 30 to 100 nm, or 100 to 600 nm, including from 40 to 80 nm, 40 to 60 nm, or from 150 to 450 nm, 400 to 700 nm, 400 to 600 nm, 300 to 800 nm, 400 to 800 nm, and 450 to 550 nm, often provide an advantage in terms of better suspension characteristics over time for an aqueous suspension of the stabilized crystals, e.g., the stabilized crystals will remain substantially completely suspended longer. Generally speaking, production of stabilized crystals by wet milling will have an MHD above 100 nm, although MHD values below 100 nm may be obtained with longer milling times and or different milling parameters. Methods such as antisolvent precipitation can produce stabilized oltipraz crystals having MHD values in ranges below 100 nm, e.g., 30-100 nm, 40-80 nm and 40-60 nm. Within the MHD range of 30 to 2000 nm are MHD ranges of from 30 to 100 nm, 40 to 80 nm, 40 to 60 nm, 100 to 250 nm, 100 to 1200 nm, 150 to 450 nm, 150 to 600 nm, 200 to 500 nm, 200 to 520, 200 to 600 nm, 300 to 600 nm, 300 to 700 nm, 300 to 800 nm, 400 to 600 nm, 400 to 700 nm, 800 nm, 500 to 750 nm, 750 to 1000 nm, 1000 to 1500 nm, and from 1500 to 2000 nm. Accordingly, the stabilized oltipraz crystals of the formulated oltipraz compositions described in this Section A typically have an intensity averaged (Z-average) MHD of from 30 to 1200 nm, such as from 100 to 600 nm, e.g. from 150 to 450 nm, 400 to 700 nm, 300 to 800 nm, 400 to 800 nm, 400 to 600 nm or 450 to 550 nm, e.g., from about 300 to 400 nm such as around 350 to 390 nm or from 400 to 600 nm such as around 500 nm, as measured by Dynamic Light Scattering.

It also is noted that the MHD measurements discussed herein also may reflect the presence of any additional ingredients such as the stabilizing agent(s) to the extent that they are present in the composition with the crystals. As used herein, however, MHD measurements obtained for complete aqueous dispersions comprising oltipraz crystals and one or more stabilizing agents, surfactants or other ingredients in the aqueous dispersion are deemed to be MHD measurements of the crystals themselves. MHD can be determined by DLS as described in the '1312 PCT, the disclosure of which relating to determining MHD by DLS is expressly incorporated herein by reference.

MHD can be determined by DLS using an appropriate instrument, e.g., a Malvern Zetasizer Nano-ZSP, using routine methods known to those skilled in the art. For example, the crystals can be put into an aqueous suspension with deionized water to a concentration of 0.01-0.1 mg (based on the weight of oltipraz) per mL prior to analysis. The result will be a transparent orange-red suspension. A backscatter (173°) detector can be used. The temperature should be set to 25° C. and samples equilibrated for 90 seconds prior to analysis. The duration, number of runs, attenuator setting, and focal position can be set automatically by the software. MHD values can be recorded with attenuator settings of 4-6 with mean count rates of 180-500 kcps.

All calculations of crystal size discussed herein can be performed in the Malvern Zetasizer software. As noted above, average crystal sizes discussed herein are intensity-averaged mean hydrodynamic radius (Z-average). The size is calculated from the mean decay time of the autocorrelation function and the Stokes-Einstein equation. The viscosity of water at 25° C. (0.8872 cP) was used. In cases where a crystal size distribution is given, the Malvern General Purpose (normal resolution) method is used, which uses non-negative least squares (NNLS) fitting of the decay curves. The functioning of the Malvern Zetasizer can be periodically checked using 100 nm polystyrene beads calibration standard. The relaxation time in the DLS experiment is between 600 and 1500 microseconds with the preferred relaxation time between 500 and 1300 microseconds.

The size calculation for the crystal sizes reported herein is based on a cumulant method using the equation: $\Gamma q2 = D = kBT/3\pi\eta d$ where D is the diffusion coefficient calculated from the measured decay rate ($\Gamma$), $kBT/3\pi\eta d$ is the Stokes-Einstein equation, d is the particle diameter, and q is the scattering wave vector which is dependent on the specific instrument method parameters as listed above. The magnitude of the scattering wave vector is calculated according to the equation q=4 Pi (refractive index of solvent) Sin(theta/2)/wavelength. The expected delay time will change if a different instrument uses a different value of q. For calculations used herein, theta=173deg, a refractive index of 1.333 for water is used, a laser wavelength of 633 nm yields a value for q=0.0264 nm^(-1).

As discussed above, the inherent variability of the wet milling process means that the size of individual crystals in any given quantity of crystals will vary and thus a quantity of crystals prepared according to this disclosure can be characterized by a distribution of crystals of varying sizes. One measure of the distribution of sizes is the polydispersity index (PdI) of the crystals in the quantity. The formula for determining PdI is:

$$PdI=(\sigma/d)^2$$

where $\sigma$ is the standard deviation and d is the mean hydrodynamic diameter (Z-average) is less than 0.80, wherein $PdI=(\sigma/d)^2$, wherein $\sigma$ is the standard deviation and d is the mean hydrodynamic diameter (Z-average). Lower values of PdI indicate a more uniform distribution of crystals in a given quantity of crystals. Typically, oltipraz crystals or quantities of such crystals in accordance with this Section A can have a PdI of less than 1, usually less than 0.8, often less than 0.6; for example between 0.10 and 0.60, e.g. between 0.10 and 0.45, such as between 0.1 and 0.35 e.g. 0.1 and 0.25. Certain embodiments of quantities of crystals in accordance with this Section A can have a PdI of less than 1, less than 0.8, less than 0.6, e.g., between 0.10 and 0.60, and between 0.10 and 0.45, 0.1 and 0.35 and 0.1 and 0.25.

Typically, therefore, oltipraz crystals prepared as discussed in this Section A will have an intensity averaged (Z-average) MHD (as measured by Dynamic Light Scattering) of from 30 to 1200 nm, wherein the PdI of the crystals is from 0.1 to 0.6. More typically such oltipraz crystals will have an intensity averaged (Z-average) MHD of from about 100 to about 800 nm, wherein the PdI of the crystals is from 0.1 to 0.45. Still more typically such oltipraz crystals having an intensity averaged (Z-average) MHD of from about 150 to about 450 nm, 300 to 800 nm, 400 to 600 nm, or 450 to 550 nm, wherein the PdI of the crystals is from 0.1 to 0.6, or from 0.1 to 0.35.

2. Dry Compositions Comprising Stabilized Oltipraz Crystals

As discussed above, the liquid compositions comprising crystals in suspension described in this Section A can be admixed with a bulking agent and then spray dried, lyophilized or otherwise processed to remove the water and/or other liquid solvent to form a dry composition. The resulting dry composition can comprise particles that largely comprise the bulking agent and thus can be much larger than the stabilized oltipraz crystals. For example, particles up to 200 microns (200,000 nm) or larger may be obtained. If desired, the size of the particles obtained from processes such as spray drying may be measured by scanning electron microscopy, laser diffraction or light microscopy. Dry compositions of crystals prepared according to this Section A generally will be in the form of an orange-red powder and can be prepared with no discolorations or large particles or chinks visible.

a. Bulking Agents

The presence of a bulking agent reduces the likelihood of crystal-crystal surface contact in a dry composition such as a spray-dried or lyophilized powder, as direct contact can make the crystals harder to re-suspend where the ultimate use of the composition is resuspension in a liquid composition. Bulking agents that are generally very soluble in water may be able to release the crystals as individual crystals upon resuspension. Accordingly, bulking agents that are very soluble in water are typically used in compositions described in this Section A. Those skilled in the art are capable of choosing appropriate bulking agents based on the particular composition and intended route of delivery. Furthermore, because the bulking agent can be such a large fraction of the overall dry composition product of crystals, its properties may affect the rate of resuspension in water as well as potentially influence the taste of the composition if administered orally, possibly significantly.

One factor that can be evaluated to determine if a particular bulking agent is appropriate for a particular embodiment includes whether the bulking agent does not alter the initial size of the stabilized oltipraz crystals in suspension prior to removal of water, e.g., through spray dying or lyophilization. Where the intended use of the dry composition is resuspension with water or other liquid to make a liquid composition for oral or other form of administration, then advantageously, a bulking agent is typically chosen that (i) does not yield large particles of precipitate upon resuspension with water, (ii) does not yield a dry powder that dissolves too slowly upon mixing with water, and (iii) yields a dry powder that is relatively stable to handling and storage, e.g., is not hygroscopic such that handling of the dry composition becomes difficult. Surface active agents may be added to the formulation, either in the liquid compositions discussed above or to the dry composition in order to enhance such properties in the dry composition. Such properties may be less important, however, if the dry composition is to be formulated into a pill, tablet, capsule, gel capsule or the like for oral administration. Where the intended use of the dry composition is oral administration such as in a pill, tablet or capsule, then the bulking agent also should be evaluated on its ability to provide the desired pharmacological profile following administration. If the smaller oltipraz crystalline drug particles coated with a stabilizing agent are adsorbed onto the larger particles of the bulking agent during blending or granulation, such as roller compaction, fluid bed, or high shear, then a water soluble bulking agent such as mannitol, or insoluble agent such as microcrystalline cellulose, may act as a carrier for those particles and aid the rate of dissolution from a capsule or a tablet.

As noted above, in principle, a bulking agent also can act as a stabilizing agent. Examples of bulking agents include, but are by no means limited to, the group consisting of polyvinylpyrrolidones (e.g., PVP K30 and PVP-VA64), cellulosic polymers such as HPC, HPMC, HPMC E3, Trehalose, and Dextrans such as Dextran 10 or Dextran 40. Examples of bulking agents such as PVP-VA64 and HPC EF that provide acceptable results for certain embodiments of this disclosure are provided herein. Most typically the bulking agent is PVP-VA64. Sometimes it is preferable that the bulking agent is not Dextran 40. As noted above, appropriate bulking agents or combinations of bulking agents can be determined for a particular composition and route of delivery. Factors such as the intended route of administration of the crystals (e.g., whether the crystals are to be administered in a dry form such as a pill or capsule or resuspended with a liquid such as water), all may be considered in determining one or more acceptable bulking agents for a particular embodiment. Other factors such as the size and amounts of crystals, type and quantity of stabilizing agent used (if any), the surfactants and amounts thereof (if any) that are employed, the amount of bulking agent to be used, the total solids in the liquid composition, the liquids in the composition and any resuspension, and the process for removing water (and/or other liquid), also may be taken into account in determining acceptable bulking agents or combinations of bulking agents.

In some circumstances use of Dextran 10 may provide a dry composition that provides particle sizes that are too large upon resuspension in water. In other embodiments, HPMC may provide a composition that dissolves more slowly than desired upon resuspension with water. In some embodiments, Trehalose can provide a composition that is more hygroscopic than desired for routine handling. Special packaging or the addition of desiccant may be used to maintain the low water content of such hygroscopic pharmaceutical compositions during stability on the shelf. Accordingly, it is sometimes preferable that the bulking agent is not dextran 10 and/or is not HPMC and/or is not trehalose. In different embodiments however, e.g., with different stabilizing agents, surfactants, or for a different intended route of administration, such bulking agents can provide acceptable compositions.

Within the aqueous or liquid compositions described in this Section A, depending on the amount of liquid used, the bulking agent(s) can comprise from about 1 to 40% by weight or more of the composition. Within such ranges are, e.g., 1 to 5%, 5 to 10%, 10 to 15%, 10 to 20%, 15 to 20%, 15 to 25%, 20 to 25%, 20 to 30%, 25 to 30%, 25 to 35%, 30 to 35%, 30 to 40%. Depending on the method chosen for removing water, the total solids in the composition may have to be maintained below a certain level to facilitate processing to a dry composition, e.g., in certain embodiments, below 30%, or about 28%, and thus the amount of bulking agent(s) used may be limited by such considerations. In certain embodiments, therefore, the bulking agent can comprise between 15% and 25%, e.g., about 20 or 21%. Accordingly, the bulking agent(s) typically comprise from about 1 to about 40 wt % of the liquid composition, such as from about 10 to about 30 wt % e.g. from about 15 to about 25 wt % such as from about 20 to about 21 wt %.

Alternatively, as with the other ingredients, the amount of bulking agent can be calculated as a percent of the solids, i.e., the non-solvent components. As a percent of the solids, the bulking agent(s) can be present in amounts by weight ranging from less than 40% up to 98% or more, e.g., 40 to 50%, 50 to 60%, 55 to 65%, 60 to 70%, 60 to 75%, 60 to 80%, 65 to 75%, 65 to 80%, 70 to 80%, 75 to 85%, 75 to 90%, 80 to 90%, 80 to 95%, 85 to 95%, 90 to 98%, and greater than 98% by weight. In certain embodiments, the bulking agent(s) can comprise between 65 and 80% by weight of the total solids, e.g., between about 70 and 78%, e.g., about 74% by weight of the total solids. Accordingly, the bulking agent(s) typically comprise from about 40 to about 90 wt % of the non-solvent (i.e., solid) composition, such as from about 65 to about 80 wt % e.g. from about 70 about 78 wt % such as from about 73 to about 75 wt %. Such amounts will also correspond to the amounts of the bulking agent(s) in the dry composition.

The compositions of crystals of oltipraz described in this Section A thus can have a MHD of from about 30 to about 2000 nm as measured by dynamic light scattering, wherein the crystals typically have a solubility in water at 20° C. of from about 3.5 to about 8 µg/ml. More typically such compositions of crystals of oltipraz have an MHD of from about 100 to about 800 nm as measured by dynamic light scattering, wherein the crystals typically have a solubility in water at 20° C. of from about 4.5 to about 7 µg/ml. Still more typically such compositions of crystals of oltipraz have a MHD of from 150 to about 450 nm, 400 to 700 nm, 400 to 600 nm, or 450 to 550 nm, as measured by dynamic light scattering, wherein the crystals typically have a solubility in water at 20° C. of from about 5 to about 6.5 µg/ml Thus, for example, a liquid composition is provided according to this Section A, wherein:
the composition comprises between about 1 to about 40 wt % of oltipraz crystals, based on the weight of the liquid composition;

the non-solvent components in the composition typically comprise from about 1 to about 70 wt % oltipraz crystals; and the composition comprises (i) from about 5 to about 40 wt % (based on the weight of solid components in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components in the composition) of one or more of sodium lauryl sulfate, a poloxamer such as Pluronic F-68 and polysorbate 80.

Thus, for example, another liquid composition is provided according to this Section A, wherein:

the composition comprises between about 4 to about 15 wt % of oltipraz crystals, based on the weight of the liquid composition;

the non-solvent components in the composition typically comprise from about 50 to about 60 wt % oltipraz crystals;

the composition comprises (i) from about 20 to about 35 wt % (based on the weight of solid components in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components in the composition) of one or more of sodium lauryl sulfate, a poloxamer such as Pluronic F-68 and polysorbate 80;

the liquid solvent is water or an aqueous buffer solution; and the composition optionally comprises from 0.1 to 1 wt % of poly(dimethylsiloxane) or silicon dioxide (simethicone) based on the non-solvent components in the composition.

Thus, for example, another liquid composition is provided according to this Section A, wherein:

the composition comprises between about 7 to about 10 wt % of oltipraz crystals, based on the weight of the liquid composition;

the non-solvent components in the composition typically comprise from about 55 to about 58 wt % oltipraz crystals;

the composition comprises (i) from about 25 to about 30 wt % (based on the weight of solid components in the composition) of one or more of a copovidone such as PVP-VA64 and a polymethacrylate-based copolymer such as EUDRAGIT® RL; and/or (ii) from about 14 to about 15 wt % % (based on the weight of solid components in the composition) of polysorbate 80 (Tween 80);

the liquid solvent is water; and the composition optionally comprises 0.1 to 1 wt % simethicone based on the non-solvent components in the composition.

The liquid composition comprising oltipraz crystals but not comprising a bulking agent is typically suitable for milling.

For example, another liquid composition is provided according to this Section A, wherein:

The concentration of oltipraz crystals in the liquid is from about 0.1 to about 10 wt % based on the weight of the liquid composition;

the non-solvent components in the composition typically comprise from about 0.5 to about 25 wt % oltipraz crystals;

the composition comprises (i) from about 5 to about 40 wt % (based on the weight of solid components excluding bulking agents in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components excluding bulking agents in the composition) of one or more of sodium lauryl sulfate, a poloxamer such as Pluronic F-68 and polysorbate 80; and the composition comprises from about 1 to about 40 wt % (based on the overall weight of the composition) of a bulking agent selected from polyvinylpyrrolidones (e.g., PVP K30 and PVP-VA64), cellulosic polymers such as HPC, HPMC, HPMC E3, Trehalose, Dextrans (such as Dextran 10 or Dextran 40), PVP-VA64 and HPC EF.

For example, another liquid composition is provided according to this Section A, wherein:

The concentration of oltipraz crystals in the liquid is from about 1 to about 6 wt % based on the weight of the liquid composition;

the non-solvent components in the composition typically comprise from about 5 to about 20 wt % oltipraz crystals;

the composition comprises (i) from about 20 to about 35 wt % (based on the weight of solid components excluding bulking agents in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components excluding bulking agents in the composition) of one or more of sodium lauryl sulfate, a poloxamer such as Pluronic F-68 and polysorbate 80;

the composition comprises from about 10 to about 30 wt % (based on the overall weight of the composition) of a bulking agent selected from PVP-VA64 and HPC EF;

the liquid solvent is water or an aqueous buffer solution; and the composition optionally comprises from 0.1 to 1 wt % of poly(dimethylsiloxane) or silicon dioxide (simethicone) based on the non-solvent components (excluding the bulking agent) in the composition.

For example, another liquid composition is provided according to this Section A, wherein:

The concentration of oltipraz crystals in the liquid is from about 2 to about 5 wt % based on the weight of the liquid composition;

the non-solvent components in the composition typically comprise from about 10 to about 18 wt % oltipraz crystals;

the composition comprises (i) from about 25 to about 30 wt % (based on the weight of solid components excluding bulking agents in the composition) of one or more of a copovidone such as PVP-VA64 and a polymethacrylate-based copolymer such as EUDRAGIT® RL; and/or (ii) from about 14 to about 15 wt % % (based on the weight of solid components excluding bulking agents in the composition) of polysorbate 80 (Tween 80);

the composition comprises from about 15 to about 25 wt % (based on the overall weight of the composition) of a bulking agent which is PVP-VA64;

the liquid solvent is water; and the composition optionally comprises 0.1 to 1 wt % simethicone based on the non-solvent components (excluding the bulking agent) in the composition.

The liquid composition comprising oltipraz crystals and a bulking agent according to this Section A is typically suitable for drying e.g. spray-drying.

Thus, for example, this Section A provides dry compositions comprising oltipraz crystals and a bulking agent, wherein:

The percentage of oltipraz in the composition (i.e. the drug loading) is from about 12 to about 20 wt %;

the composition comprises (i) from about 5 to about 40 wt % (based on the weight of solid components excluding bulking agents in the composition) of one or more of acrylate- and alkenyl ether-based co-polymers, polyvinylpyrrolidone, hydroxypropylcellulose, hydroxypropyl methylcellulose, a copovidone such as PVP-VA64, and a polymethacrylate-based copolymer such as EUDRAGIT® RL; and/or (ii) from about 10 to about 20 wt % % (based on the weight of solid components excluding bulking agents in the composition) of one or more of sodium lauryl sulfate, a poloxamer such as Pluronic F-68 and polysorbate 80; and the composition comprises from about 40 to about 90 wt % (based on the overall weight of the composition) of a bulking agent selected from polyvinylpyrrolidones (e.g., PVP K30 and PVP-VA64), cellulosic polymers such as HPC, HPMC, HPMC E3, Trehalose, Dextrans (such as Dextran 10 or Dextran 40), PVP-VA64 and HPC EF.

For example, another dry composition comprising oltipraz crystals and a bulking agent is provided by this Section A, wherein:

The percentage of oltipraz in the composition (i.e. the drug loading) is from about 14 to about 18 wt %;

the composition comprises (i) from about 20 to about 35 wt % (based on the weight of solid components excluding bulking agents in the composition) of one or more of a polymethacrylate-based copolymer such as Eudragit RL, an acrylate- and alkenyl ether-based co-polymer such as Carbopol 974P NF; a polyvinylpyrrolidone such as PVP (K15 or K-30); a hydroxypropylcellulose such as HPC EF and a hydroxypropyl methylcellulose such as HPMC E3; and/or (ii) from about 12 to about 18 wt % % (based on the weight of solid components excluding bulking agents in the composition) of one or more of sodium lauryl sulfate, a poloxamer such as Pluronic F-68 and polysorbate 80;

the composition comprises from about 65 to about 80 wt % (based on the overall weight of the composition) of a bulking agent selected from PVP-VA64 and HPC EF; and the composition optionally comprises from 0.1 to 1 wt % of poly(dimethylsiloxane) or silicon dioxide (simethicone) based on the weight of solid components excluding bulking agents in the composition For example, another dry composition comprising oltipraz crystals and a bulking agent is provided by this Section A, wherein:

The percentage of oltipraz in the composition (i.e. the drug loading) is from about 15 to about 17 wt %;

the composition comprises (i) from about 25 to about 30 wt % (based on the weight of solid components excluding bulking agents in the composition) of one or more of a copovidone such as PVP-VA64 and a polymethacrylate-based copolymer such as EUDRAGIT® RL; and/or (ii) from about 14 to about 15 wt % % (based on the weight of solid components excluding bulking agents in the composition) of polysorbate 80 (Tween 80); and the composition comprises from about 70 to about 78 wt % (based on the overall weight of the composition) of a bulking agent which is PVP-VA64; and the composition optionally comprises 0.1 to 1 wt % simethicone based on the weight of solid components excluding bulking agents in the composition.

The dry compositions described above can be suspended in liquid to form a liquid suspension; typically the weight ratio of the solid:liquid is from about 1:10 to 1:200 such as from about 1:20 to 1:150 e.g. 1:30 to 1:100.

The stabilized oltipraz crystals in the liquid compositions described in this Section A typically retain a MHD of from 30 to 1200 nm for at least 1 hour; more typically the stabilized oltipraz crystals retain a MHD of from 100 to 800 nm for at least 6 hours; still more typically the stabilized oltipraz crystals retain a MHD of from 150 to 450 nm, 400 to 800 nm, 400 to 600 nm, or 450 to 550 nm for at least 24 hours.

The stabilized oltipraz crystals in the solid compositions described in this Section A typically have a solubility in water at 20° C. of from about 3.5 to about 8 µg/ml, more typically from about 4.5 to about 7 µg/ml, still more typically from about 5 to about 6.5 µg/ml.

3. Methods of Making Compositions Comprising Oltipraz Crystals

Methods of making the formulated oltipraz compositions described in this Section A are described in the '1312 PCT and typically provide advantages due to their scalability. The disclosure of such methods of making in the '1312 is expressly incorporated herein by reference. Such methods include wet milling, or other methods, e.g., antisolvent precipitation, supercritical fluid precipitation, fluid bed granulation, wet-impregnation, evaporation (e.g., rotary evaporation, vacuum drying) or other known means of producing compositions comprising particles having an MHD in the size ranges described herein. Stabilizing agents may be added as in the wet milling process and removal of liquids may still be necessary.

As discussed in the '1312 PCT, once the target MHD of the stabilized oltipraz crystals is reached, all or a portion of the suspension then may be mixed with one or more bulking agents as described above. The resulting mixture may be further diluted as desired to achieve the desired target solids content prior to further processing to remove the water and/or other liquid from the composition. The final suspension may be stirred prior to the step of removing the liquid.

Where the liquid of the composition is water, known processes such as spray drying or lyophilization may be used to remove the water from the composition. An exemplary spray-drying process is provided in Example 1 of the '1312 PCT and described below. The resulting composition then may be further processed as desired. The powder is preferably stable for a minimum period of time, e.g., at least one month, at least two months, at least three months, or at least six months, one year, two years, or more than two years. Stability of the powder may be measured at room temperature (e.g., 70° F. or 21° C.) or at a temperature below room temperature (e.g., 5° C.) or at a higher temperature and relative humidity, e.g., 40° C. and 75% RH. Stability of the powder may be measured according to a number of parameters, including purity, potency, or ability to re-suspend and remain substantially re-suspended in a liquid composition (see, e.g., Example 4 of the '1312 PCT, which is expressly incorporated herein by reference).

The '1312 PCT also provides the parameters that may need to be considered and adjusted to achieve acceptable or optimal results when milling and spray drying are employed in combination, including throughput, nozzle and drying gas flow rate, time, and milling machinery and parameters. Such disclosure in the '1312 PCT is expressly incorporated herein by reference.

As noted therein, for a given target crystal size, one of ordinary skill can find a combination of wet-milling machinery and wet-milling media that can achieve the target crystal size.

B. Pharmaceutical Compositions and Administration of Formulated Oltipraz Compositions The formulated oltipraz compositions described above in Section A can be administered in a dry or liquid pharmaceutical composition. Other agents for treating a viral infection, e.g., an infection caused by a coronavirus such as one associated with MERS or SARS (e.g., SARS-CoV-2, including type L and type S strains), One or more additional agents or known antiviral agents (e.g., remdesivir) can be co-administered together with the pharmaceutical compositions comprising the formulated oltipraz crystals. Co-administration can occur at the same or different times.

The formulated oltipraz compositions described in Section A above may be used to formulate various kinds of pharmaceutical preparations that may be used alone or in conjunction with another pharmaceutically active agent. The preparations typically comprise a dry composition as described above. Practically speaking, pharmaceutical compositions comprising the dry composition can comprise any amount of the stabilized oltipraz crystals. The amount of the composition will depend on the desired dosage of the oltipraz and the concentration of the oltipraz in the dry composition. In certain embodiments, for example, the dry composition comprises a single dose of up to 5000 mg, e.g., 100 to 500 mg, 500 to 1000 mg, 1000 to 1500 mg, and 1500 to 2000 mg, 2000 to 2500 mg, 2500 mg to 3000 mg, 3000 mg to 4000 mg and 4000 mg to 5000 mg. The dose may thus be from 100 to 5000 mg such as from 500 to 4000 mg, such as from 1000 to 3000 mg e.g. from 1500 to 2000 mg. Single dosage amounts over 5000 mg also may be employed. Within such ranges are exemplary amounts of up to 600 mg of a dry composition as described above, up to 500 mg of a dry pharmaceutical composition, up to 400 mg of a dry pharmaceutical composition, up to 350 mg of a dry composition, or up to 300 mg of a dry composition as described herein. Exemplary amounts within such ranges also include 250 mg, 300 mg, 350, mg, 400 mg, 450 mg, 500 mg, 550 mg, 600 mg, 650 mg, 700 mg, 750 mg, 800 mg, 850 mg, 900 mg, 950 mg and 1000 mg, 1100 mg, 1200 mg, 1300 mg, 1400 mg, 1500 mg, 1600 mg, 1700 mg, 1800 mg, 1900 mg and 2000 mg. As described above, such dry pharmaceutical compositions can comprise from 5% to over 25% of oltipraz crystals. For example, if the dry composition comprises 5% oltipraz crystals, then the foregoing dosages comprise up to 250 mg of oltipraz. If the dry composition comprises 15% oltipraz crystals, then the foregoing dosages comprise up to 750 mg of oltipraz, and if the dry composition comprises 25% oltipraz crystals, then the foregoing dosages comprise up to 1250 mg of oltipraz.

Dry pharmaceutical compositions also may tend to be fairly electrostatic and so including a small amount of one or more pharmaceutically acceptable lubricants, e.g., magnesium stearate or silica oxide, can assist in the process of metering out quantities of the dry composition. Other processing techniques such as granulation, for example, roller compaction, high shear or fluid bed, may also be used to produce larger particles with binders or other pharmaceutical excipients that are more easily processed and still have rapid dissolution and greater solubility.

In certain embodiments, a dry composition of oltipraz crystals prepared according to Section A above may be re-suspended in water and/or other liquid for oral administration as a liquid composition in a weight:weight ratio, of 1 part of dry composition and an amount of water of from less than 10 parts of water (or other liquid) up to 200 parts or more of water (or other liquid). Within such ranges include, e.g., 1-10, 10-20, 20-30, 30-40, 40-50, 50-60, 60-7, 70-80, 80-90, 90-100, 100-125, 125-150, 150-175, 175-200, or more than 200 parts of water (or other liquid) per part of dry composition. The ratio of dry composition to liquid can therefore be from 1:10 to 1:200 such as from 1:20 to 1:150 e.g. 1:30 to 1:100 such as 1:40 to 1:70 e.g. about 1:50 to 1:60. As noted above, where the composition is prepared using at least one stabilizing agent, the MHD of the crystals in the composition may remain within the target range for a period of time, e.g., at least 1 hour, at least 3 hours, at least 6 hours, at least 12 hours or at least 24 hours, or longer. Further, depending on the combinations of stabilizing agent(s), if any, and bulking agent (if any) and crystal size, the re-suspended composition also may readily dissolve, e.g., with vigorous shaking for less than 15 minutes, less than 10 minutes, less than 5 minutes, less than three minutes, less than 2 minutes less than one minute, or less than 30 seconds, and also may remain substantially homogeneously suspended for a period of time, e.g., for at least 1 hour, at least 3 hours, at least 6 hours, at least 12 hours, or at least 24 hours. A suspension of oltipraz crystals may be deemed to be substantially homogeneous if the concentration of oltipraz in a test sample taken from the top of the liquid composition after a defined period of time (e.g., less than 1 minute, 1 minute, 2 minutes, 5 minutes, 10 minutes, or 15 minutes) comprises a desired minimum target percentage of the original concentration, e.g., at least 85%, 90%, 95% or 98% of the concentration of oltipraz in a sample taken from the liquid composition immediately after the composition is resuspended to form a substantially homogeneous composition.

Formulations of the pharmaceutical compositions for oral administration also may be presented as a mouthwash, or a carbonated liquid, or an oral spray or aerosol, or an oral ointment, gel, or cream. Liquids suitable for preparing compositions comprising the stabilized oltipraz crystals for buccal administration, may include buccal vehicle components known to the art. In other embodiments, the oral formulations of compositions comprising the stabilized oltipraz crystals may be emulsions or suspensions.

Liquid dosage forms useful for oral administration of compositions comprising the stabilized oltipraz crystals include pharmaceutically acceptable emulsions, microemulsions, suspensions, syrups and elixirs. In addition to the active ingredients, the liquid dosage forms may contain inert diluents commonly used in the art. Besides inert diluents, the oral compositions can also include adjuvants such as wetting agents, emulsifying and suspending agents, sweetening, flavoring, coloring, perfuming and preservative agents. Compositions for oral administration may include additional components, such as coloring agents, flavoring agents, fragrances, antimicrobial agents, or sweetening agents as further described.

Examples of suitable aqueous and nonaqueous carriers that may be employed in the pharmaceutical compositions comprising the stabilized oltipraz crystals include water, ethanol, and polyols.

Alternative embodiments of pharmaceutical compositions suitable for oral administration of compositions comprising formulated oltipraz compositions include but are not limited to compositions in the form of capsules (including sprinkle capsules and gelatin capsules), sachets, stickpacks, pills, tablets, and lozenges.

C. Devices for Oral Administration

In certain embodiments, liquid formulations of the compositions comprising the stabilized oltipraz crystals may be prepared and administered using a device that facilitates administration of a single dose of the pharmaceutical composition. Such devices, which are known in the art and described in the '1312 PCT, can include a cavity or reservoir where a dry composition and a liquid such as water and/or a non-aqueous solvent may be mixed and then administered to the patient via an opening in the device. The disclosure in the '1312 PCT relating to such devices is expressly incorporated herein by reference. Typically, such devices comprise a cavity and a compartment that is separate from the cavity, in which compartment a dry powder can reside. At the time of administration, the powder is released from the compartment into the cavity or reservoir. In some devices, this is accomplished by breaking a barrier that separates the compartment from the cavity or reservoir. Thereafter, the powder may be mixed, typically by shaking, with a liquid in the cavity that may have been added earlier or at the time. The cavity is of sufficient size to hold both the dry pharmaceutical composition and a quantity of liquid comprising an amount of water and/or non-aqueous solvent sufficient to permit mixing of the dry pharmaceutical composition to form a liquid composition. The liquid may be added to the container at the time of packaging to create a self-contained product comprising both dry composition and liquid that may be mixed together at the time of administration. Alternatively, the container can contain only a dry pharmaceutical composition and the liquid is then added prior to administration. The liquid may contain flavoring additives as discussed below. Alternatively, other types of packaging that separate the dry and liquid ingredients may be used. For example, the powder and the liquid can be sealed in 2 form-fill-and-seal pouches, either side by side or one on top of the other and separated by a rupturable seal. The person administering the drug would then rupture the seal and mix the contents back and forth between the 2 compartments until dissolved or suspended.

Once the composition is substantially homogeneous (e.g., from the shaking), it is then administered to the patient via an opening in the device created, e.g., by uncoupling a portion of the device to expose the cavity containing the liquid mixture. For example, a portion of the device, e.g., the top, can be removed by unscrewing a threaded portion from another threaded portion of the container to expose the cavity containing the liquid mixture, which then may be administered to the patient or by the patient. Examples of such devices are provided in U.S. Pat. No. 6,148,996, U.S. application 20080202949, and U.S. Pat. No. 3,156,369.

Such single-use devices can be employed for orally administering liquid compositions described herein, especially for prophylaxis or treatment of oral mucositis or its symptoms as described below.

The disclosure thus also provides a kit comprising (i) compositions comprising a formulated oltipraz composition and (ii) a device for oral administration of such compositions. The kit optionally further contains instructions for use.

For such devices, the formulated oltipraz composition may be in a dry form. In such instances, the dry composition which can be present, e.g., in a compartment as described above, is admixed with water and/or other liquid solvent prior to administration (e.g., by exposing the dry composition to the liquid and shaking) as discussed above.

D. Compositions for Topical Administration

In some embodiments, the formulated oltipraz composition may be suitable for topical administration, e.g., as a crème, gel or lotion, and may include moisturizers, humectants and other additives well known in the art for topical compositions. Topical compositions also may be delivered transdermally via a patch that is applied over the skin, and such patches are well known in the art.

E. Compositions for Rectal/Colonic Delivery

In certain embodiments, the pharmaceutical compositions described in Section B above can be formulated for rectal administration to provide colon-specific delivery using known methods and compositions. Generally speaking, delivery of pharmaceutical composition via rectal administration route can be achieved by using suppositories, enemas, ointments, creams or foams. Suppositories are among the most common rectal dosage forms, and bases are generally fatty in nature, but water-soluble or water-miscible bases can also be utilized. In order to achieve a desirable bioavailability the active ingredient should come in contact with the rectal or colonic mucosa.

F. Compositions and Devices for Inhalation Administration

In other embodiments, pharmaceutical compositions described above in Section B may be delivered via the respiratory tract by providing the composition in inhalable form, e.g., in an inhaler device, either in dry powder form or in a liquid carrier. For example, inhalable compositions can comprise the active ingredient in dry powder compositions provided in dry powder inhalers. See, e.g., WO2014177519 and US20140065219. Alternatively, inhalable compositions can comprise the active ingredient in a liquid carrier such as ethanol. See, e.g., EP2536412 A2.

The disclosure thus also provides a kit comprising (i) a pharmaceutical composition as described in Section B above, and (ii) a device for administering such composition by inhalation. The kit optionally further contains instructions for use.

G. Methods of Treating

In certain embodiments, the pharmaceutical compositions and devices for oral administration described in Sections B through F above may be used for treating a human or non-human animal patient in need. The patient typically will be a human patient, although the pharmaceutical compositions of this disclosure can be used for treating non-human animals, e.g., for veterinary uses.

The formulated oltipraz compositions described herein can be used for prophyaxis or the treatment of a patient who has a viral infection, including an infection caused by a coronavirus such as one associated with MERS or SARS (e.g., SARS-CoV-2, including type L and type S strains), including treating a patient with mild illness symptoms, with the goal of preventing progression into severe disease.

The formulated oltipraz compositions described herein thus can be used to treat an individual who has a viral infection, including, e.g., one that is caused by a coronavirus such as one associated with MERS or SARS (e.g., SARS-CoV-2, including type L and type S strains), Treatment with such compositions can reduce the maximum severity of one or more symptoms experienced by the individual if taken if taken prior to or at the outset of the infection, and/or reduce or eliminate one or more of the symptoms and/or effects if taken after the viral infection has begun. Alternatively, or in addition, the pharmaceutical formulations, compositions, devices and therapies described herein may be used to pre-treat an individual who is at risk of a viral infection such as a coronavirus infection, e.g., one associated with MERS or SARS (e.g., SARS-CoV-2, including type L and type S strains) in order to lessen the likelihood that an infection may occur or to prepare the individual to better withstand a viral infection if it does occur. Such "host hardening" in advance of a viral infection can reduce the severity of, or eliminate, some or all of the effects and/or symptoms experienced by the individual in the event that he/she experiences a viral infection such as COVID-19. Such pre-treatment can be especially beneficial for persons at risk from such viral infections e.g., individuals having hypertension, decreased pulmonary function, or respiratory diseases or conditions such as pneumonia.

The pharmaceutical compositions comprising formulated oltipraz compositions thus may be administered to accomplish one, more than one, or all of the following beneficial effects on human or non-human animal patients who are suffering from a viral infection, e.g., caused by a coronavirus such as one associated with MERS or SARS (e.g., SARS-CoV-2, including type L and type S strains): (i) lessen, reduce or eliminate one, more than one, or all of fever, cough, shortness of breath, perspiration, difficulty breathing, persistent pain or pressure in the chest, new confusion or inability to arouse and bluish lips or face, or (ii) treat an individual who is at risk of a viral infection such as a coronavirus infection, e.g., such as one associated with MERS or SARS (e.g., SARS-CoV-2, including type L and type S strains) in order to prepare the individual to better withstand a viral infection if it occurs in order to reduce or eliminate one, more than one, or all of fever, cough, shortness of breath, perspiration, difficulty breathing, persistent pain, liver failure, kidney failure, hypercoagulability, encephalitis, or pressure in the chest, new confusion or inability to arouse and bluish lips or face in the event that the subject is infected with a coronavirus such as one associated with MERS or SARS (e.g., SARS-CoV-2, including type L and type S strains). A pharmaceutical compositions comprising formulated oltipraz may also be administered to increase the blood oxygen saturation levels ($SpO_2$ or $PaO_2$) of individuals experiencing respiratory distress (e.g., resulting from viral infection such influenza or a corona virus pathogenic to humans like SARS-CoV-2) relative to their $SpO_2$ or $PaO_2$ level prior to receiving the formulated oltipraz or relative individuals experiencing respiratory distress (e.g., resulting from the same type of viral infection) who have not received formulated oltipraz. As noted above, administering such pharmaceutical compositions can be especially beneficial for individuals at risk from viral infections caused by a coronavirus such as such as one associated with MERS or SARS (e.g., SARS-CoV-2, including type L and type S strains), e.g., individuals having hypertension, decreased pulmonary function, and/or respiratory diseases or conditions such as pneumonia. The disclosure also provides the use of a pharmaceutical composition as described herein in the manufacture of a medicament for the treatment of persons who have such viral infections or who are at risk for such viral infections.

The pharmaceutical compositions and devices for administration comprising formulated oltipraz compositions as described in Sections B through F may be co-administered with other drugs (e.g., separately or as an admixture) that are useful in order to lessen, reduce or eliminate the effects and/or symptoms associated with the viral infections such as those described above. Such potential drugs include remdesivir, hydroxychloroquine and chloroquine.

Typically, the pharmaceutical composition(s) is/are provided to the patient in an effective amount. The term "effective amount" is used herein to refer to an amount of the therapeutic composition sufficient to produce a significant biological response, e.g., a significant decrease in one, more than one, or all of the effects and/or symptoms experienced by the individual in the event that he/she experiences a viral infection such as one associated with MERS or SARS (e.g., SARS-CoV-2, including type L and type S strains), e.g., fever, cough, shortness of breath, perspiration, difficulty breathing, persistent pain or pressure in the chest, new confusion or inability to arouse and bluish lips or face. Actual dosage levels of the pharmaceutical compositions comprising formulated oltipraz compositions can be varied so as to administer an amount that is effective to achieve the desired therapeutic response for a particular subject and/or application. Of course, the effective amount in any particular case will depend upon a variety of factors including formulation, route of administration, combination with other drugs or treatments, severity of the condition being treated, and the physical condition and prior medical history of the subject being treated.

As used herein, the term "subject" includes both human and animal subjects, and thus veterinary therapeutic uses are provided in accordance with this disclosure. The terms "treatment" or "treating" relate to any treatment of a condition of interest (e.g., a viral infection such as such as one associated with MERS or SARS (e.g., SARS-CoV-2, including type L and type S strains), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

EXAMPLE

Certain embodiments of this disclosure are further illustrated by the following example, which should not be construed as limiting in any way.

Example 1: Method for Manufacturing an Oltipraz Composition

A pharmaceutical composition comprising oltipraz, stabilizing agents polysorbate 80 and Eudragit RL, and a bulking polymer, polyvinylpyrrolidone vinylacetate (PVP-VA64), was manufactured by the following steps.

In an appropriately sized container with agitator, formulation components were added in the following order: stabilizing polymer, purified water, polysorbate 80, then oltipraz. The mixture was stirred to create a homogeneous suspension vehicle. The composition of the suspension vehicle prior to milling is shown in Table 2. The suspension vehicle was milled in a temperature-controlled grinding chamber (such as a Dyno-mill, model KDL) with 0.5 mm yttrium-stabilized zirconium oxide spheres as a grinding media. A list of additional mill parameters is shown in Table 3. Total milling time of the suspension was 270 minutes, determined based on a target mean residence time of 7 minutes in the grinding chamber (see Equation 1). The MHD of the crystals/particles in the milled suspension was measured by dynamic light scattering (DLS) performed as described above and was 330 nm.

The milled suspension was transferred to a new, appropriately sized solution tank, bulking polymer PVP-VA64 was added, and then additional purified water to dilute the suspension to 28% total solids. The final suspension composition shown in Table 4 was then stirred for at least 30 minutes. The suspension was spray dried with a Niro PSD-1 spray dryer using parameters shown in Table 5. Spray dried powder was collected in a cyclone.

TABLE 2

Composition of Suspension Vehicle

| Component | Function | Composition (weight percent of suspension) |
| --- | --- | --- |
| Eudragit RL | Stabilizing agent | 4.3 |
| Polysorbate 80 | Stabilizing agent | 2.1 |
| Oltipraz | Active | 8.6 |
| Water, USP Purified | Solvent | 85.0 |

TABLE 3

Parameters Used with the Dyno-mill KDL

| Parameter | Value |
| --- | --- |
| Chamber size | 0.6 L |
| Agitator Paddles | 64 mm |
| Gap size | 0.2 mm |
| Rotor Speed | Approximately 3000 rpm (belt position 3) |
| Mill mode | Continuous |
| Grinding media volume | 2000 g |
| Suspension Temperature (Reservoir) | 2.0-40.0° C. |
| Suspension Temperature (Mill outlet) | 2.0-40.0° C. |
| Suspension Flow Rate | 500 mL/min |
| Mill Run Time | 270-300 minutes |

Example Calculation for Total Required Milling Time of Suspension Vehicle.

$$\frac{\text{Working chamber volume}}{F} * \text{total mill time} = 7 \text{ minutes}$$

$$\text{where } F = \frac{\text{total suspension mass}}{\text{suspension density}}$$

Working chamber volume was defined as the empty chamber volume minus the volume of the grinding media.

TABLE 4

Composition of Spray Suspension

| Component | Function | Composition (% of suspension) |
| --- | --- | --- |
| Milled Suspension (from Table 1) | — | 48.7 |
| PVP-VA 64 | Bulking polymer | 20.7 |
| Water, USP Purified | Solvent | 30.6 |

TABLE 5

Spray Drying Process Conditions on a PSD-1 Scale Spray Dryer

| Process Condition | Value |
| --- | --- |
| Atomizer | Spray Systems 2-fluid 2850/120 |
| Atomization gas pressure (psig) | 20 |
| Drying-gas inlet temperature (° C.) | 105 |
| Drying-gas outlet temperature (° C.) | 50 |
| Solution flow rate (g/min) | 35 |
| Drying-gas flow rate (g/min) | 1850 |

The spray dried powder was analyzed to confirm the powder re-suspended in water within 2 minutes, and the resulting oltipraz milled crystal size was similar to the original crystal size achieved during the milling step. Two tests were performed: first, the powder was re-suspended in water at an oltipraz concentration of 5 mg/mL and the time to uniform suspension by visual observation was recorded. Second, the resulting crystal size of the suspension was measured by DLS. The spray dried powder re-suspended in water with vigorous shaking within 2 minutes, and the resulting suspension crystal size was 370 nm which was similar to the original milled suspension crystal size.

Recitation of Embodiments

1. A method of treating a human or non-human animal patient who has a viral infection or is at risk of incurring a viral infection comprising administering a pharmaceutical composition, wherein the composition comprises a quantity of stabilized oltipraz crystals having an intensity averaged, mean hydrodynamic diameter (Z-average) ("MHD") of from 30 to 2000 nm,
    wherein the MHD is determined by performing dynamic light scattering at 25° C. on a suspension of the crystals in water at a concentration of 0.01 to 0.1 mg of crystals per mL of water.
2. A method according to embodiment 1, wherein the quantity substantially comprises crystals that have a MHD in the range of from 200 to 1000 nm.
3. A method according to embodiment 1 or 2, wherein the quantity substantially comprises crystals that have a MHD in the range of from 300 to 800 nm.
4. A method according to embodiment 2, wherein the composition comprises at least one stabilizing agent, and wherein the quantity substantially comprises crystals that will have a MHD in the range of from 200 to 1000 nm if left in water at 25° C. for or an amount of time selected from the group consisting of 1 hour, 6 hours, 12 hours and 24 hours.
5. A method according to embodiment 3, wherein the composition comprises at least one stabilizing agent, and wherein the quantity substantially comprises crystals that will have a MHD in the range of from 300 to 800 nm if left in water at 25° C. for an amount of time selected from the group consisting of 1 hour, 6 hours, 12 hours and 24 hours.
6. A method according to any of embodiments 1-5, wherein the composition comprises less than 1 percent of drug-degradant impurities relative to 4-methyl-5-(pyrazin-2-yl)-3H-1,2-dithiole-3-thione in the aqueous composition and less than 2 percent total impurities relative to the 4-methyl-5-(pyrazin-2-yl)-3H-1,2-dithiole-3-thione in the aqueous suspension.
7. A method according to any of embodiments 1-6, wherein the composition comprises less than 0.1 percent of drug-degradent impurities relative to 4-methyl-5-(pyrazin-2-yl)-3H-1,2-dithiole-3-thione in the aqueous composition and less than 0.5 percent total impurities relative to the 4-methyl-5-(pyrazin-2-yl)-3H-1,2-dithiole-3-thione in the aqueous suspension.
8. A method according to any of embodiments 1-7, wherein the polydispersity index (PdI) of the crystals in the quantity is less than 0.80, wherein $PdI=(\sigma/d)^2$, wherein $\sigma$ is the standard deviation and d is the mean hydrodynamic diameter (Z-average).
9. A method comprising a quantity of crystals according to embodiment 8, wherein the polydispersity index (PdI) of the crystals in the quantity is less than 0.60.
10. A method comprising a quantity of crystals according to embodiment 8, wherein the polydispersity index (PdI) of the crystals in the quantity is between 0.10 and 0.60.
11. A method comprising a quantity of crystals according to embodiment 8, wherein the polydispersity index (PdI) of the crystals in the quantity is between 0.10 and 0.45.
12. A method according to any of embodiments 1-11, wherein the quantity of crystals comprises substantially the entire quantity of 4-methyl-5-(pyrazin-2-yl)-3H-1,2-dithiole-3-thione present in the composition.
13. A method according to any of embodiments 5-12, wherein the stabilized oltipraz crystals are stabilized by at least one stabilizing agent that comprises a polymer.
14. A method according to embodiment 13, wherein the polymer is a cationic or anionic polymer.
15. A method according to embodiment 14, wherein the polymer is a cationic polymer.
16. A method according to embodiment 15, wherein the cationic polymer comprises ammonium functionality.
17. A method according to embodiment 16, wherein the cationic polymer comprises quaternary ammonium functionality.
18. A method according to any of embodiments 15-17, wherein the cationic polymer is a polymer that is formed from polymerization of compounds comprising at least one acrylate-containing compound.
19. A method according to any of embodiments 15-18, wherein the cationic polymer comprises Poly(ethyl acrylate-co-methyl methacrylate-co-trimethylammonioethyl methacrylate chloride) 1:2:0.2 (Eudragit RL).
20. A method according to any of embodiments 1-19, wherein the stabilized oltipraz crystals are stabilized by at least one stabilizing agent that comprises a surfactant.
21. A method according to embodiment 20, wherein the surfactant is a nonionic surfactant.
22. A method according to embodiment 21, wherein the surfactant is a sorbitan ester.
23. A method according to any of embodiments 20-22, wherein the surfactant is polyethylene glycol sorbitan monooleate.
24. A method according to embodiment 20, wherein the surfactant is selected from the group consisting of poly-ethylene glycol sorbitan monooleate surfactants, polyethylene glycol hydrogenated castor oil, block copolymers of poly(ethylene oxide) and poly(propylene oxide), sodium lauryl sulfate, benzalkonium chloride, and sodium docusate.
25. A method according to any of embodiments 1-24, wherein the composition comprises a bulking agent.
26. A method according to any of embodiments 1-25, wherein the stabilized oltipraz crystals are stabilized by at least one stabilizing agent that comprises a bulking agent.
27. A method according to any of embodiments 25 or 26, wherein the bulking agent comprises a polyvinylpyrrolidone compound.
28. A method according to embodiment 27, wherein the bulking agent comprises a copolymer of polyvinylpyrrolidone and poly(vinyl acetate) with a ratio of approximately 6:4 of vinylpyrrolidone and vinyl acetate monomers (PVP-VA64).
29. A method according to any of embodiments 1-28, wherein the composition comprises water.
30. A method according to any of embodiments 1-28, wherein the composition comprises a non-aqueous solvent.
31. A method according to any of embodiments 1-28, wherein the composition substantially excludes water, and wherein the composition is capable of forming a substantially complete aqueous suspension of a quantity of crystals.
32. A method according to embodiment 31, wherein the composition will form a substantially complete aqueous suspension with vigorous shaking in less than a period of time selected from the group consisting of 15 minutes, 10 minutes, 5 minutes, 2 minutes and 1 minute, if mixed with water at a weight:weight ratio of 1 part of the dry composition per 10 parts of water at 25° C.
33. A method according to any of embodiments 1-32, wherein the pharmaceutical composition is administered to a human patient at risk of a viral infection to reduce the risk that the patient will be infected and/or to reduce the maximum severity of one or more symptoms experienced if the patient becomes infected.
34. A method according to any one of embodiments 33, wherein the viral infection is one that is caused by a coronavirus.
35. A method according to embodiment 34, wherein the coronavirus is associated with MERS or SARS.
36. A method according to embodiment 34, wherein the coronavirus is a SARS-CoV-2 coronavirus.
37. A method according to any of embodiment 33-36, wherein the patient has one or more of hypertension, decreased pulmonary function, and a respiratory disease or condition such as pneumonia.
38. A method according to any of embodiments 33-37, wherein the pharmaceutical composition is administered to a human patient that has a viral infection to reduce or eliminate one or more symptoms associated with the viral infection.
39. A method according to any one of embodiments 38, wherein the viral infection is one that is caused by a coronavirus.
40. A method according to embodiment 39, wherein the coronavirus is associated with MERS or SARS.
41. A method according to embodiment 39, wherein the coronavirus is a SARS-CoV-2 coronavirus.
42. A method according to any of embodiments 38-41, wherein administration reduces or eliminates one or more symptoms associated with the viral infection selected from the group consisting of fever, cough, shortness of breath, perspiration, difficulty breathing, persistent pain or pressure in the chest, new confusion or inability to arouse, pathologically low blood oxygen saturation levels (e.g., less than 90%, 92%, 94%, or 95% saturation $PaO_2$ or $SpO_2$ as measured by pulse oximetry), and bluish lips or face.

43. A method according to any of embodiment 38-42, wherein the patient has one or more of hypertension, decreased pulmonary function, decreased $PaO_2$ or $SpO_2$ values (e.g., less than 90%, 92%, 94%, or 95% saturation), and a respiratory disease or condition such as pneumonia.

44. A method according to any of embodiments 1-43, where the pharmaceutical composition is a suspension that is administered orally using a pharmaceutically acceptable container according to Section C of this disclosure.

45. A method according to embodiment 44, wherein the liquid pharmaceutical composition is formed from the step of admixing a dose of a dry pharmaceutical composition according to embodiment 31 or 32, and a liquid.

46. A method according to embodiments 44 or 45, wherein the liquid further comprises at least one pharmaceutically acceptable taste-modifying additive.

47. A method according to embodiment 45 or 46, wherein the step of admixing is carried out by shaking the container for a period of time selected from the group consisting of ten minutes or less, five minutes or less, three minutes or less, and one minute or less.

Definitions

For convenience, certain terms employed in the specification and appended claims are collected here. These definitions should be read in light of the entire disclosure and understood as by a person of skill in the art.

The articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, processes described herein and claimed below can include steps in addition to the steps recited, and the order of the steps or acts of the process is not necessarily limited to the order in which the steps or acts of the process are recited. In the context of this disclosure, the words "process" and "method" are synonymous.

In the claims, as well as in the specification, all transitional phrases such as "comprising," "comprised of" "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Those skilled in the art will recognize, or will be able to ascertain using no more than routine experimentation, many equivalents to the specific embodiments described herein. Such equivalents are intended to be encompassed by the following claims.

What is claimed is:

1. A method of treating a human or non-human animal patient who has a coronavirus infection to reduce the severity of, or eliminate, some or all of the effects and/or symptoms experienced by the human or non-human animal patient who has a coronavirus infection, comprising administering to the human or non-human animal patient a pharmaceutical composition, wherein the composition comprises a quantity of stabilized oltipraz crystals having an intensity averaged, mean hydrodynamic diameter (Z-average) ("MHD") of from 30 to 2000 nm in the presence of any additional ingredients, thereby treating the patient who has a coronavirus infection;

wherein the MHD is determined by performing dynamic light scattering on a Malvern Zetasizer Nano-ZSP equipped with a 173° backscatter detector at 25° C. on a suspension of the crystals in water at a concentration of 0.01 to 0.1 mg of crystals per mL of water following 90 seconds of equilibration of the crystals in the water prior to measurement of the MHD.

2. The method of claim 1, wherein the quantity of stabilized oltipraz crystals substantially comprises crystals that have a MHD in the range of from 200 to 1000 nm.

3. The method of claim 1, wherein the quantity of stabilized oltipraz crystals substantially comprises crystals that have a MHD in the range of from 300 to 800 nm.

4. The method of claim 2, wherein the composition comprises at least one stabilizing agent, and wherein the quantity of stabilized oltipraz crystals substantially comprises crystals that will have a MHD in the range of from 200 to 1000 nm if left in water at 25° C. for 1 hour.

5. The method of claim 3, wherein the composition comprises at least one stabilizing agent, and wherein the quantity of stabilized oltipraz crystals substantially comprises crystals that will have a MHD in the range of from 300 to 800 nm if left in water at 25° C. for 1 hour.

6. The method of claim 5, wherein the polydispersity index (PdI) of the crystals in the quantity of stabilized oltipraz crystals is less than 0.80, wherein $PdI=(\sigma/d)^2$, wherein $\sigma$ is the standard deviation and d is the mean hydrodynamic diameter (Z-average).

7. The method of claim 6, wherein the polydispersity index (PdI) of the crystals in the quantity of stabilized oltipraz crystals is between 0.10 and 0.60.

8. The method of claim 5, wherein the composition comprises water and/or a non-aqueous solvent.

9. The method of claim 5, wherein the composition substantially excludes water, and wherein the composition is capable of forming a substantially complete aqueous suspension of the quantity of stabilized oltipraz crystals with vigorous shaking in less than a period of time selected from the group consisting of 15 minutes, 10 minutes, 5 minutes, 2 minutes, and 1 minute, if mixed with water at a weight: weight ratio of 1 part of the composition per 10 parts of water at 25° C.

10. The method of claim 5, wherein the pharmaceutical composition is administered to a human patient that has a coronavirus infection to reduce the maximum severity of one or more symptoms experienced by the patient that has a coronavirus infection.

11. The method of claim 10, wherein the coronavirus infection is a SARS-CoV-2 coronavirus.

12. The method of claim 11, wherein the patient has hypertension or decreased pulmonary function.

13. The method of claim 11, wherein the patient has a respiratory disease or condition.

14. The method of claim 13, wherein the patient has pneumonia.

15. The method of claim 5, wherein the pharmaceutical composition is administered to a human patient that has a coronavirus infection to reduce or eliminate one or more symptoms associated with the coronavirus infection.

16. The method of claim 15, wherein the coronavirus infection is one that is caused by a coronavirus associated with MERS or SARS.

17. The method of claim 16, wherein the coronavirus is associated with SARS.

18. The method of claim 16, wherein the coronavirus is a SARS-CoV-2 coronavirus.

19. The method of claim 18, wherein administration reduces or eliminates one or more symptoms associated with the coronavirus infection selected from the group consisting of fever, cough, shortness of breath, perspiration, difficulty breathing, persistent pain or pressure in the chest, new confusion or inability to arouse, and bluish lips or face.

20. The method of claim 18, wherein the patient has one or more of hypertension, decreased pulmonary function, and a respiratory disease or condition.

* * * * *